US010376595B2

(12) United States Patent
Guo et al.

(10) Patent No.: US 10,376,595 B2
(45) Date of Patent: *Aug. 13, 2019

(54) TREATMENT OF INFLAMMATORY DISEASES WITH INHIBITORS OF C5A ACTIVITY

(71) Applicant: InflaRx GmbH, Jena (DE)

(72) Inventors: Renfeng Guo, Ann Arbor, MI (US); Niels C. Riedemann, Jena (DE)

(73) Assignee: InflaRx GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,340

(22) Filed: Jun. 13, 2018

(65) Prior Publication Data

US 2018/0280530 A1   Oct. 4, 2018

Related U.S. Application Data

(63) Continuation of application No. PCT/EP2018/050146, filed on Jan. 3, 2018.

(30) Foreign Application Priority Data

| Apr. 3, 2017 | (EP) | ...................................... 17164573 |
| Jun. 23, 2017 | (EP) | ...................................... 17177657 |
| Sep. 7, 2017 | (EP) | ...................................... 17189938 |

(51) Int. Cl.
| *A61K 47/68* | (2017.01) |
| *A61K 31/711* | (2006.01) |
| *A61K 39/395* | (2006.01) |
| *A61P 17/00* | (2006.01) |
| *C07K 16/18* | (2006.01) |
| *C07K 16/28* | (2006.01) |
| *C07K 16/40* | (2006.01) |
| *A61K 39/00* | (2006.01) |

(52) U.S. Cl.
CPC ........ *A61K 47/6807* (2017.08); *A61K 31/711* (2013.01); *A61K 39/3955* (2013.01); *A61P 17/00* (2018.01); *C07K 16/18* (2013.01); *C07K 16/2896* (2013.01); *C07K 16/40* (2013.01); A61K 2039/505 (2013.01); C07K 2317/24 (2013.01); C07K 2317/55 (2013.01); C07K 2317/76 (2013.01)

(58) Field of Classification Search
USPC ......................................................... 514/330
See application file for complete search history.

(56) References Cited

FOREIGN PATENT DOCUMENTS

WO   WO2016102877 A1   6/2016

OTHER PUBLICATIONS

InflaRx (InflaRx initiates exploratory Phase II trial with IFX-1, a first-in-class anti-complement C5a antibody, in patients with HS, Jan. 4, 2017) (Year: 2017).*
Bekker et. al. (Plos One (Oct. 21, 2016) 11:1-19). (Year: 2016).*
Harding, J., "Eculizumab," Drugs of the Future, Prious Science, ES., vol. 29, No. 7, Jul. 1, 2004, pp. 673-676.
Kaplan, M., "Eculizumab," Current Opinion in Investigational Drugs, Pharmapress US, vol. 3, No. 7, Jul. 1, 2002, pp. 1017-1023.
Clinicaltrials.Gov: "Archive History for NCT03001622: Studying Complement Inhibition in Patients with Moderate to Severe Hidradenitis Suppurativa," Mar. 20, 2017, (6 pages).
Eqs Group Ag, et al., "InflaRx initiates exploratory phase II trial with IFX-1, a first-in-class anti-complement C5a antibody, in patients with Hidradenitis Suppurativa—dgap. de," Jan. 4, 2017, (2 pages).
Jorizzo, J. et al., "Low-dose weekly methotrexate for unusual neutrophilic vascular reactions: Cutaneous polyarteritis nodosa and Behcets disease," Journal of the American Academy of Dermatology, Mosby Inc. US, vol. 24, No. 6, Jun. 1, 1991, pp. 973-978.
Keseroglu, H.O. et al., "A Case of Subcorneal Pustular Dermatosis Successfully Treated with Acitretin," Archives of Inflammation, vol. 1, No. 2, Oct. 27, 2016, pp. 1-3.
Dang, L. et al., "Role of the complement anaphylatoxin C5a-receptor pathway in atopic dermatitis in mice," Molecular Medicine Reports, vol. 11, No. 6, Feb. 4, 2015, pp. 4183-4189.
Ternowitz, T. et al., "Methotrexate inhibits the Human C5a-Induced Skin Response in Patients with Psoriasis," J. Invest. Dermatol., vol. 89, No. 2, Aug. 1, 1987, pp. 192-196.
Navarini, A. et al., "Neutrophilic dermatoses and autoinflammatory diseases with skin involvement—innate immune disorders," Seminars in Immopathology, vol. 38, No. 1, 2016, pp. 45-56.
Dhingra, N. et al., "Attenuated neutrophil axis in atopic dermatitis compared to psoriasis reflects TH17 pathway differences between these diseases," Journal of Allergy and Clinical Immunology, vol. 132, No. 2, Aug. 1, 2013, pp. 1-7.
Cumpelik, A. et al., "Neutrophil microvesicles resolve gout by inhibiting C5a-mediated priming of the inflammasome," Annals of the Rheumatic Diseases, vol. 75, No. 6, 2016, pp. 1236-1245.
Cugno, M. et al., PAPA, PASH and PAPASH Syndromes: Pathophysiology, Presentation and Treatment, American Journal of Clinical Dermatology, vol. 18, Feb. 25, 2017, pp. 555-562.

(Continued)

*Primary Examiner* — Marcos L Sznaidman
(74) *Attorney, Agent, or Firm* — Melissa Hunter-Ensor; Leslie Serunian

(57) ABSTRACT

The present invention relates to inhibitors of C5a activity and their use in the treatment of cutaneous, neutrophilic, inflammatory diseases in a subject.

19 Claims, 8 Drawing Sheets

Specification includes a Sequence Listing.

(56) References Cited

OTHER PUBLICATIONS

Graille, J. et al., "PAPA, PASH, PAPASH, PsAPASH, PASS . . . des syndromes auto-inflammatoires PAS si simples," Revue De Medecine Interne, vol. 36, Dec. 2015, CA206, 2 pages.
Argyropoulou, M. et al., "An Open-label Trial to Assess the Safety of IFX-1 in Patients with Hidradenitis Suppurativa Not Eligible for Adalimumab," Aug. 4, 2017, poster (1 page).
Guo, R. et al., "IFX-1 blocking the anaphylatoxin C5a—an anti-inflammatory effect in patients with hidradenitis suppurativa," Aug. 29, 2017, poster (1 page).
Notification of Transmittal of the International Search Report, International Search Report and the Written Opinion of the International Searching Authority in corresponding PCT/EP2018/050146, dated Jul. 30, 2018 (31 pages).
U.S. Pat. No. US 2017/0349575 A1 (published Jul. 12, 2017), English equivalent of (WO 2016/102877).
Response to Invitation to Pay Additional Fees in PCT/EP2018/050146, submitted to European Patent Office dated Apr. 27, 2018 (4 pages).
Office Action, dated May 22, 2019, in corresponding European Patent Application No. 18701250.5 (9 pages).

\* cited by examiner

SEQUENCE LISTING

<160> NUMBER OF SEQ ID NOS: 34

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 2
<211> LENGTH: 9
<212> TYPE: PRT
<213> ORGANISM: Homo sapiens

<400> SEQUENCE: 2

Asn Asp Glu Thr Cys Glu Gln Arg Ala
1               5

<210> SEQ ID NO 3
<211> LENGTH: 7
<212> TYPE: PRT
<213> ORGANISM: Homo sapiens

<400> SEQUENCE: 3

Ser His Lys Asp Met Gln Leu
1               5

<210> SEQ ID NO 4
<211> LENGTH: 7
<212> TYPE: PRT
<213> ORGANISM: Homo sapiens

```
<400> SEQUENCE: 4

Asp Glu Thr Cys Glu Gln Arg
1               5

<210> SEQ ID NO 5
<211> LENGTH: 5
<212> TYPE: PRT
<213> ORGANISM: Homo sapiens

<400> SEQUENCE: 5

His Lys Asp Met Gln
1               5

<210> SEQ ID NO 6
<211> LENGTH: 13
<212> TYPE: PRT
<213> ORGANISM: Artificial Sequence
<220> FEATURE:
<223> OTHER INFORMATION: IFX-1 CDR3 heavy chain

<400> SEQUENCE: 6

Cys Ala Arg Gly Asn Asp Gly Tyr Tyr Gly Phe Ala Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: INab708 CDR3 heavy chain

<400> SEQUENCE: 7

Cys Thr Arg Arg Gly Leu Tyr Asp Gly Ser Ser Tyr Phe Ala Tyr
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: IFX-1 CDR3 light chain

<400> SEQUENCE: 8

Cys Gln Gln Ser Asn Glu Asp Pro Tyr Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: INab708 CDR3 light chain

<400> SEQUENCE: 9

Cys Gln Gln Asn Asn Glu Asp Pro Leu Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: IFX-1 CDR2 heavy chain

<400> SEQUENCE: 10
```

```
Ile Asp Pro Ser Asp Ser Glu Ser Arg Leu Asp Gln
1               5                   10
```

<210> SEQ ID NO 11
<211> LENGTH: 12
<212> TYPE: PRT
<213> ORGANISM: Artificial Sequence
<220> FEATURE:
<223> OTHER INFORMATION: INab708 CDR2 heavy chain

<400> SEQUENCE: 11

```
Ile Leu Pro Gly Ser Gly Ser Thr Asn Tyr Asn Glu
1               5                   10
```

<210> SEQ ID NO 12
<211> LENGTH: 7
<212> TYPE: PRT
<213> ORGANISM: Artificial Sequence
<220> FEATURE:
<223> OTHER INFORMATION: IFX-1 CDR2 light chain

<400> SEQUENCE: 12

```
Ile Tyr Ala Ala Ser Asn Leu
1               5
```

<210> SEQ ID NO 13
<211> LENGTH: 7
<212> TYPE: PRT
<213> ORGANISM: Artificial Sequence
<220> FEATURE:
<223> OTHER INFORMATION: INab708 CDR2 light chain

<400> SEQUENCE: 13

```
Ile Tyr Ala Ala Ser Asn Leu
1               5
```

<210> SEQ ID NO 14
<211> LENGTH: 14
<212> TYPE: PRT
<213> ORGANISM: Artificial Sequence
<220> FEATURE:
<223> OTHER INFORMATION: IFX-1 CDR1 heavy chain

<400> SEQUENCE: 14

```
Cys Lys Ala Ser Gly Tyr Ser Phe Thr Thr Phe Trp Met Asp
1               5                   10
```

<210> SEQ ID NO 15
<211> LENGTH: 14
<212> TYPE: PRT
<213> ORGANISM: Artificial Sequence
<220> FEATURE:
<223> OTHER INFORMATION: INab708 CDR1 heavy chain

<400> SEQUENCE: 15

```
Cys Lys Ala Thr Gly Asn Thr Phe Ser Gly Tyr Trp Ile Glu
1               5                   10
```

<210> SEQ ID NO 16
<211> LENGTH: 16
<212> TYPE: PRT
<213> ORGANISM: Artificial Sequence
<220> FEATURE:
<223> OTHER INFORMATION: IFX-1 CDR1 light chain

<400> SEQUENCE: 16

```
Cys Lys Ala Ser Gln Ser Val Asp Tyr Asp Gly Asp Ser Tyr Met Lys
```

<210> SEQ ID NO 17
<211> LENGTH: 16
<212> TYPE: PRT
<213> ORGANISM: Artificial Sequence
<220> FEATURE:
<223> OTHER INFORMATION: INab708 CDR1 light chain

<400> SEQUENCE: 17

Cys Lys Ala Ser Gln Ser Val Asp Tyr Asp Gly Asp Ser Tyr Met Asn
 1               5                  10                  15

<210> SEQ ID NO 18
<211> LENGTH: 21
<212> TYPE: PRT
<213> ORGANISM: Artificial Sequence
<220> FEATURE:
<223> OTHER INFORMATION: IFX-1 FR1 heavy chain

<400> SEQUENCE: 18

Gln Val Gln Leu Gln Gln Ser Gly Pro Gln Leu Val Arg Pro Gly Thr
 1               5                  10                  15

Ser Val Lys Ile Ser
            20

<210> SEQ ID NO 19
<211> LENGTH: 15
<212> TYPE: PRT
<213> ORGANISM: Artificial Sequence
<220> FEATURE:
<223> OTHER INFORMATION: IFX-1 FR2 heavy chain

<400> SEQUENCE: 19

Trp Val Lys Gln Arg Pro Gly Gln Gly Leu Glu Trp Ile Gly Arg
 1               5                  10                  15

<210> SEQ ID NO 20
<211> LENGTH: 33
<212> TYPE: PRT
<213> ORGANISM: Artificial Sequence
<220> FEATURE:
<223> OTHER INFORMATION: IFX-1 FR3 heavy chain

<400> SEQUENCE: 20

Arg Phe Lys Asp Arg Ala Thr Leu Thr Val Asp Lys Ser Ser Ser Thr
 1               5                  10                  15

Val Tyr Met Gln Leu Ser Ser Pro Thr Ser Glu Asp Ser Ala Val Tyr
            20                  25                  30

Tyr

<210> SEQ ID NO 21
<211> LENGTH: 11
<212> TYPE: PRT
<213> ORGANISM: Artificial Sequence
<220> FEATURE:
<223> OTHER INFORMATION: IFX-1 FR4 heavy chain

<400> SEQUENCE: 21

Trp Gly Gln Gly Thr Leu Val Thr Val Ser Ser
 1               5                  10

<210> SEQ ID NO 22
<211> LENGTH: 22
<212> TYPE: PRT

```
<213> ORGANISM: Artificial Sequence
<220> FEATURE:
<223> OTHER INFORMATION: IFX-1 FR1 light chain

<400> SEQUENCE: 22

Asp Ile Val Leu Thr Gln Ser Pro Ala Ser Leu Ala Val Ser Leu Gly
1               5                   10                  15

Gln Arg Ala Thr Ile Ser
            20

<210> SEQ ID NO 23
<211> LENGTH: 13
<212> TYPE: PRT
<213> ORGANISM: Artificial Sequence
<220> FEATURE:
<223> OTHER INFORMATION: IFX-1 FR2 light chain

<400> SEQUENCE: 23

Trp Tyr Gln Gln Lys Pro Gly Gln Pro Pro Lys Leu Leu
1               5                   10

<210> SEQ ID NO 24
<211> LENGTH: 33
<212> TYPE: PRT
<213> ORGANISM: Artificial Sequence
<220> FEATURE:
<223> OTHER INFORMATION: IFX-1 FR3 light chain

<400> SEQUENCE: 24

Gln Ser Gly Ile Pro Ala Arg Phe Ser Gly Ser Gly Ser Gly Thr Asp
1               5                   10                  15

Phe Thr Leu Asn Ile His Pro Val Glu Glu Glu Asp Ala Ala Thr Tyr
            20                  25                  30

Tyr

<210> SEQ ID NO 25
<211> LENGTH: 10
<212> TYPE: PRT
<213> ORGANISM: Artificial Sequence
<220> FEATURE:
<223> OTHER INFORMATION: IFX-1 FR4 light chain

<400> SEQUENCE: 25

Phe Gly Gly Gly Thr Lys Leu Glu Ile Lys
1               5                   10

<210> SEQ ID NO 26
<211> LENGTH: 20
<212> TYPE: PRT
<213> ORGANISM: Artificial Sequence
<220> FEATURE:
<223> OTHER INFORMATION: INab708 FR1 heavy chain

<400> SEQUENCE: 26

Val Gln Leu Leu Glu Ser Gly Ala Glu Leu Met Lys Pro Gly Ala Ser
1               5                   10                  15

Val Lys Ile Ser
            20

<210> SEQ ID NO 27
<211> LENGTH: 15
<212> TYPE: PRT
<213> ORGANISM: Artificial Sequence
<220> FEATURE:
<223> OTHER INFORMATION: INab708 FR2 heavy chain
```

```
<400> SEQUENCE: 27

Trp Val Lys Gln Arg Pro Gly His Gly Leu Glu Trp Ile Gly Glu
1               5                   10                  15

<210> SEQ ID NO 28
<211> LENGTH: 33
<212> TYPE: PRT
<213> ORGANISM: Artificial Sequence
<220> FEATURE:
<223> OTHER INFORMATION: INab708 FR3 heavy chain

<400> SEQUENCE: 28

Lys Phe Lys Gly Lys Ala Thr Leu Thr Ala Asp Thr Ser Ser Asn Thr
1               5                   10                  15

Ala Tyr Met Gln Leu Ser Ser Leu Thr Ser Glu Asp Ser Ala Val Tyr
                20                  25                  30

Tyr

<210> SEQ ID NO 29
<211> LENGTH: 11
<212> TYPE: PRT
<213> ORGANISM: Artificial Sequence
<220> FEATURE:
<223> OTHER INFORMATION: INab708 FR4 heavy chain

<400> SEQUENCE: 29

Trp Gly Gln Gly Thr Leu Val Thr Val Ser Ala
1               5                   10

<210> SEQ ID NO 30
<211> LENGTH: 22
<212> TYPE: PRT
<213> ORGANISM: Artificial Sequence
<220> FEATURE:
<223> OTHER INFORMATION: INab708 FR1 light chain

<400> SEQUENCE: 30

Asp Ile Val Leu Thr Gln Ser Pro Ala Ser Leu Ala Val Ser Leu Gly
1               5                   10                  15

Gln Arg Ala Thr Ile Ser
            20

<210> SEQ ID NO 31
<211> LENGTH: 13
<212> TYPE: PRT
<213> ORGANISM: Artificial Sequence
<220> FEATURE:
<223> OTHER INFORMATION: INab708 FR2 light chain

<400> SEQUENCE: 31

Trp Tyr Gln Gln Lys Pro Gly Gln Pro Pro Lys Leu Leu
1               5                   10

<210> SEQ ID NO 32
<211> LENGTH: 33
<212> TYPE: PRT
<213> ORGANISM: Artificial Sequence
<220> FEATURE:
<223> OTHER INFORMATION: INab708 FR3 light chain

<400> SEQUENCE: 32

Gly Ser Gly Ile Pro Ala Arg Phe Ser Gly Ser Gly Ser Gly Thr Asp
1               5                   10                  15
```

```
Phe Thr Leu Asn Ile His Pro Val Glu Glu Val Ala Ala Thr Tyr
                20                  25                  30
Tyr

<210> SEQ ID NO 33
<211> LENGTH: 10
<212> TYPE: PRT
<213> ORGANISM: Artificial Sequence
<220> FEATURE:
<223> OTHER INFORMATION: INab708 FR4 light chain

<400> SEQUENCE: 33

Phe Gly Ala Gly Thr Leu Leu Glu Leu Lys
1               5                   10

<210> SEQ ID NO 34
<211> LENGTH: 40
<212> TYPE: RNA
<213> ORGANISM: Artificial Sequence
<220> FEATURE:
<223> OTHER INFORMATION: pegylated mixed L-RNA/DNA-aptamer NOX-D21
<220> FEATURE:
<221> NAME/KEY: misc_feature
<222> LOCATION: (1)..(1)
<223> OTHER INFORMATION: substituted by 40 kDaPEG-aminohexyl-
<220> FEATURE:
<221> NAME/KEY: misc_feature
<222> LOCATION: (7)..(7)
<223> OTHER INFORMATION: desoxy uridine
<220> FEATURE:
<221> NAME/KEY: misc_feature
<222> LOCATION: (28)..(28)
<223> OTHER INFORMATION: desoxy uridine
<220> FEATURE:
<221> NAME/KEY: misc_feature
<222> LOCATION: (38)..(38)
<223> OTHER INFORMATION: desoxy cytidine

<400> SEQUENCE: 34
gcgauguggu ggugaagggu uguugggugu cgacgcacgc                              40
```

TREATMENT OF INFLAMMATORY DISEASES WITH INHIBITORS OF C5A ACTIVITY

CROSS REFERENCE TO RELATED APPLICATIONS

This application is a Track One continuation application of International PCT Application No. PCT/EP2018/050146, filed Jan. 3, 2018, which claims priority to European Patent Application Nos. EP 17164573.2, filed Apr. 3, 2017; EP 17177657.8, filed Jun. 23, 2017; and EP 17189938.8, filed Sep. 7, 2017. This application claims priority to and the benefit of the aforementioned patent applications, the contents of all of which are incorporated herein by reference.

FIELD OF THE INVENTION

The present invention relates to inhibitors of C5a activity and their use in the treatment of cutaneous, neutrophilic, inflammatory diseases in a subject.

BACKGROUND OF THE INVENTION

Target C5a in Inflammation

C5a is a 74 amino acid spanning split product of its "mother molecule" C5 and represents one endpoint of the complement activation cascade. It can be generated through activation of at least three well-described pathways (the alternative, the classical and the MBL pathway). All pathways merge at the level of C3, forming the C5- or alternative C5 convertase leading to cleavage of C5 into C5a and C5b. The latter binds with C6, C7, C8 and multiple C9 molecules ultimately leading to formation of pores in e.g. bacterial membranes (terminal Membrane Attack Complex=MAC). C5a is generated when the complement system is activated in settings of inflammation and other immunological and inflammatory disorders/diseases.

Among the complement activation products, C5a is one of the most potent inflammatory peptides, with a broad spectrum of functions (Guo and Ward, 2005). C5a exerts its effects through the high-affinity C5a receptors (C5aR and C5L2) (Ward, 2009). C5aR belongs to the rhodopsin family of G-protein-coupled receptors with seven transmembrane segments; C5L2 has a similar structure but appears not to be G-protein-coupled. It is currently believed that C5a exerts its biological functions primarily through C5a-C5aR interaction, as few biological responses have been found for C5a-C5L2 interaction. However, latest reports demonstrate signaling also through C5L2 activation (Rittirsch and others, 2008).

C5aR is widely expressed on myeloid cells including neutrophils, eosinophils, basophils, and monocytes, and non-myeloid cells in many organs, especially in the lung and liver, indicative of the importance of C5a/C5aR signaling. Widespread up-regulation of C5aR expression occurs during the onset of sepsis, and blockade of C5a/C5aR interaction by anti-C5a, or anti-C5aR antibodies, or C5aR antagonists renders highly protective effects in rodent models of sepsis (Czermak and others, 1999; Huber-Lang and others, 2001; Riedemann and others, 2002).

C5a has a variety of biological functions (Guo and Ward, 2005). C5a is a strong chemoattractant for neutrophils and also has chemotactic activity for monocytes and macrophages. C5a causes an oxidative burst ($O_2$ consumption) in neutrophils and enhances phagocytosis and release of granular enzymes. C5a has also been found to be a vasodilator. C5a has been shown to be involved in modulation of cytokine expression from various cell types and to enhance expression of adhesion molecule expression on neutrophils. High doses of C5a can lead to nonspecific chemotactic "desensitization" of neutrophils, thereby causing broad dysfunction. Many inflammatory diseases are attributable to the effects of C5a, including sepsis, acute lung injury, inflammatory bowel disease, rheumatoid arthritis and others. In the experimental setting of sepsis, exposure of neutrophils to C5a can lead to neutrophil dysfunction and paralysis of signaling pathways, leading to defective assembly of NADPH oxidase, paralysis of MAPK signaling cascades, a great depression of oxidative burst, phagocytosis and chemotaxis (Guo and others, 2006; Huber-Lang and others, 2002). Thymocytes apoptosis and delayed neutrophil apoptosis are two important pathogenic events for sepsis development, which are dependent on the presence of C5a. During experimental sepsis, C5a up-regulates $\beta 2$-integrin expression on neutrophils to promote cell migration into organs, one of the major causes for multi-organ failure (MOF). It is also found that C5a is attributable to the activation of the coagulation pathway that occurs in experimental sepsis. C5a stimulates the synthesis and release from human leukocytes of pro-inflammatory cytokines such as TNF-$\alpha$, IL-$1\beta$, IL-6, IL-8, and macrophage migration inhibitory factor (MIF). Given that complement activation is an event occurring during the onset of acute inflammation, C5a may come into play before emergence of most of the inflammatory "cytokine storm". It appears that C5a plays a key role in orchestrating and amplifying the performance of the cytokine network and the formation of systemic inflammatory response syndrome (SIRS).

In the immunological regulatory network tailing to the adaptive immunity, C5a affects the crosstalk between dendritic cells (DC) and $\delta\epsilon T$ cells, and this may result in a large production of inflammatory mediators such as IL-17 (Xu and others, 2010). An essential role for C5a has been established and defined in the generation of pathogenic Th17 responses in systemic lupus erythematosus (SLE) (Pawaria and others, 2014). In addition, it has been reported that C5a is a key regulator for Treg cells offering a powerful suppressive effect for Treg propagation and induction (Strainic and others, 2013). Given the fact that Treg and TH17 are the essential players in the autoimmune disease setting, inhibition of C5a signaling would be expected to significantly reduce overactive immune status in the autoimmune diseases.

IFX-1

IFX-1 is a chimeric monoclonal IgG4 antibody which specifically binds to the soluble human complement split product C5a. IFX-1 is composed of 1328 amino acids and has an approximate molecular weight of 148,472 Daltons. The CDR and FR sequences of IFX-1 are disclosed in Table 3 below.

IFX-1 is expressed in a mammalian CHO cell line as recombinant protein and finally formulated in a phosphate buffered saline solution for intravenous administration. The binding of this antibody to human C5a facilitates a highly effective blockade of C5a-induced biological effects by disabling C5a binding to and reacting with its corresponding cell-bound receptors.

Various nonclinical studies were conducted to assess pharmacological and toxicological aspects of IFX-1, which can be divided into in vitro/ex vivo tests and in vivo studies including GLP toxicology studies in cynomolgus monkey (using IFX-1). None of the conducted nonclinical tests and studies revealed any toxicological or safety concerns for IFX-1. Human Phase I trial indicated that safety laboratory parameters, vital signs and ECG parameters showed no clinically relevant time or dose-related changes.

In vitro analysis of IFX-1 demonstrates a strong binding capacity to soluble human C5a as well as a high blocking activity of C5a-induced biological effects such as lysozyme release from human neutrophils or CD11b up-regulation in neutrophils in human whole blood. One IFX-1 antibody reaches the capability of neutralizing the effects of 2 molecules C5a with close to 100% efficiency in experimental in vitro settings. Clinical trials with IFX-1 have been ongoing to test its clinical efficacy in several inflammatory diseases including septic organ dysfunction and complex cardiac surgery.

Neutrophils

Neutrophils, terminally differentiated cells with a short lifespan in circulation, are the most abundant leukocytes in the human body. As a first line of defense against invading microorganisms, neutrophils are characterized by their ability to act as phagocytic cells, release lytic enzymes from their granules and produce reactive oxygen species upon stimulation. In addition to microbial products, other stimuli such as immune complex can also induce the respiratory burst in neutrophils, leading to enhanced inflammation and the recruitment of inflammatory cells (Kaplan, 2013).

After infiltrating into inflamed tissues, neutrophils engage in many other cell types, such as macrophages, dendritic cells (DCs), natural killer cells, lymphocytes and mesenchymal stem cells, regulate innate and adaptive immune responses. For instance, neutrophils can modulate DC maturation and the proliferation and polarization of T cells, and they can also directly prime antigen-specific T-helper type 1 and T-helper type 17 cells (Abi Abdallah and others, 2011). A variety of stimuli induce neutrophil degranulation, including C5a, formyl-methionyl-leucyl-phenylalanine (FMLP), lipopolysaccharide, platelet activating factor, and Tumor necrosis factor (TNF) (Kaplan, 2013). The contents released from degranulation and oxidative species together with cytokines and chemokines resulted from neutrophil activation are the primary inflammatory mediators that cause tissue damage, and this mechanism is believed to be attributable to many types of inflammatory tissue injury.

Hidradenitis Suppurativa (HS)

HS is a chronic devastating skin disorder affecting areas rich in apocrine glands, and it is considered as one of neutrophil-associated cutaneous inflammatory diseases. Nodules appear in the affected areas, and they progressively become swollen and rupture with the release of pus. This process occurs repeatedly leading to sinus tract formation and scars (Jemec, 2004). This disease course creates a frustrating situation for the patients but also for physicians. The point prevalence is reported to range between 1% and 4% (Jemec and others, 1996).

The exact pathophysiology of HS is not well defined. Smoking, dietary habits and genetic predisposition have all been linked with HS (Kurzen and others, 2008; Slade and others, 2003). The percentage of NK cells was increased and that of CD4-lymphocytes decreased compared to healthy controls probably implying the existence of an autoimmune predilection for the disorder. IL-1β and IL-17 have been found to be upregulated in the lesion of HS, being associated with the activation of inflammasome (Lima and others, 2016). Hidradenitis suppurativa (HS) is presented with the high number of neutrophil infiltrates in the inflamed skin, especially in the late stage of disease (Lima and others, 2016; Marzano, 2016). Activated neutrophils could be an important effector cell type causing tissue damage through direct harmful effect or indirect regulatory effect toward other effect cells such as active T cells and TH17 in this disease setting.

A hypothesis for the implication of some autoimmune or autoinflammatory mechanism in the pathogenesis of HS has been created over the last years. The hypothesis is further reinforced by positive results from the administration of TNF antagonists in prospective, placebo-controlled studies, which result in the approval of Adalimumab (an antibody directed against tumor necrosis factor α) in patients with moderate to severe HS. One major, yet unanswered question is how neutrophils are recruited to the affected skin lesion and to what extent activated neutrophils would contribute to the disease development.

The wide range of possible pathogenic mechanisms suggested by different studies may imply that HS is associated with host mechanisms rather than exogenous factors. Taking into account of the paradox that both anti-infectious (antibiotics) and pro-infectious (anti-TNF, corticosteroids, immunosuppressive drugs) therapies may be helpful, HS may appear as an auto-inflammatory disease based on a defect in the hair follicle innate immunity (Revuz, 2009), which is supported by the fact that pro-inflammatory cytokines such as interleukin (IL)-1β, and tumor necrosis factor-α (TNF-α) are markedly increased in lesional and perilesional skin (Wollina and others, 2013).

Neutrophilic Dermatoses

The neutrophilic dermatoses (ND) are a group of disorders characterized by skin lesions for which histologic examination reveals intense inflammatory infiltrates composed primarily of neutrophils with no evidence of infection. ND mainly include Sweet syndrome (SS), pyoderma gangrenosum (PG), subcorneal pustular dermatosis (SPD), other well-defined entities, and their atypical or transitional forms (Prat and others, 2014). Hidradenitis suppurativa (HS) has recently been assigned to the family of ND based on the high number of neutrophil infiltrates observed in the inflamed skin (Lima and others, 2016; Marzano, 2016).

Pyoderma gangrenosum (PG) and hidradenitis suppurativa (HS) are prototypic neutrophilic dermatoses that are regarded as autoinflammatory disease in origin with the hallmark of the accumulation of neutrophils in the skin (Braun-Falco and others, 2012; Marzano and others, 2014). Autoinflammatory Syndrome represents an emerging group of inflammatory conditions that are distinct from autoimmune, allergic, and infectious disorders. From a pathophysiological perspective, all the autoinflammatory syndromes such as PAPA (pyogenic arthritis, PG and acne), PASH (PG, acne and hidradenitis suppurativa) or PAPASH (pyogenic arthritis, acne, PG and hidradenitis suppurativa) share common mechanisms consisting of over-activation of the innate immune system and 'sterile' neutrophil-rich cutaneous inflammation (Cugno and others, 2017).

Neutrophils and Autoimmune Diseases

Autoimmune diseases are defined by defective differentiation of self and non-self molecules, leading to inappropriate recognition of self molecules and tissues as foreign structures, and concomitant immune attack against host organs. The pathogenesis of autoimmune diseases can generally be divided into two phases, immunization phase and effector phase. Immunization phase is characterized by the emergence of autoreactive T-lymphocytes. Those T-cells then trigger a secondary response leading to tissue damaging phase by activating various other cell types (B-cells, cytotoxic T-cells, NK-cells, neutrophils, macrophages, osteoclasts, fibroblasts, etc.). The activation of those effector cells by the autoreactive T cells can be considered as the effector phase which can be mediated by multiple levels including autoantibody production, cytokine networks or direct cell-cell contacts (Nemeth and Mocsai, 2012).

The role of neutrophils in the pathophysiological development of autoimmune diseases has been limitedly defined, but increasingly appreciated. Neutrophils could participate in the multiple steps of the autoimmune disease process, including antigen presentation, regulation of the activity of other immune cell types, and direct tissue damage. Neutrophils can expose/release autoantigens when activated, or when dying by apoptosis, or during formation of neutrophil extracellular traps (NETs). They can also contribute to tissue deposition of autoantibodies or, as an effector cell type, they can induce tissue damage themselves. Accumulative studies have demonstrated that neutrophils play an active role in the development of autoimmune diseases, such as, rheumatoid arthritis (RA), systemic lupus erythematosus (SLE), bullous pemphigoid, epidermolysis bullosa acquisita, ANCA-associated vasculitis, familial Mediterranean fever, cryopyrin-associated periodic disorders (CAPS) and gout, etc. (Nemeth and Mocsai, 2012; Nemeth and others, 2016). As the skin being an easy target for immune responses, cutaneous inflammation is one of most frequent syndromes presented by these autoimmune diseases.

TECHNICAL PROBLEMS UNDERLYING THE PRESENT INVENTION

As explained above, there existed a need in the prior art for effective therapies for the treatment of neutrophilic dermatoses, such as Hidradenitis suppurativa (HS), and cutaneous neutrophilic autoimmune diseases.

The present inventors have now surprisingly found that molecules inhibiting C5a signaling, e.g. an anti-C5a antibody, are exceptionally well-suited for the treatment of Hidradenitis suppurativa. The present inventors have additionally studied the physiological mechanism leading to neutrophil activation and found out that C5a is the key driver of neutrophil activation.

Thus, the present inventors expect that inhibiting C5a activity will be a suitable therapy approach for the treatment of various neutrophilic disorders, especially cutaneous, neutrophilic, inflammatory diseases.

SUMMARY OF THE INVENTION

In a first aspect the present invention relates to a compound for use in the treatment of a cutaneous, neutrophilic, inflammatory disease in a subject, wherein the compound is an inhibitor of C5a activity, and wherein the cutaneous, neutrophilic, inflammatory disease is selected from the group consisting of hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); neutrophilic panniculitis; familial Mediterranean fever, cryopyrin-associated disorders, gout, and Schnitzler syndrome.

In a second aspect, the present invention relates to a method for the treatment of a cutaneous, neutrophilic, inflammatory disease in a subject, comprising the step of:
administering to a subject in need thereof a therapeutic amount of a compound, wherein the compound is an inhibitor of C5a activity, and wherein the cutaneous, neutrophilic, inflammatory disease is selected from the group consisting of hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); neutrophilic panniculitis; familial Mediterranean fever, cryopyrin-associated disorders, gout, and Schnitzler syndrome.

In a third aspect, the present invention relates to a use of a compound for the preparation of a pharmaceutical composition for the treatment of a cutaneous, neutrophilic, inflammatory disease, wherein the compound is an inhibitor of C5a activity, and wherein the cutaneous, neutrophilic, inflammatory disease is selected from the group consisting of hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); neutrophilic panniculitis; familial Mediterranean fever, cryopyrin-associated disorders, gout, and Schnitzler syndrome.

This summary of the invention does not necessarily describe all features of the present invention. Other embodiments will become apparent from a review of the ensuing detailed description.

DETAILED DESCRIPTION OF THE INVENTION

Definitions

Figure 1:
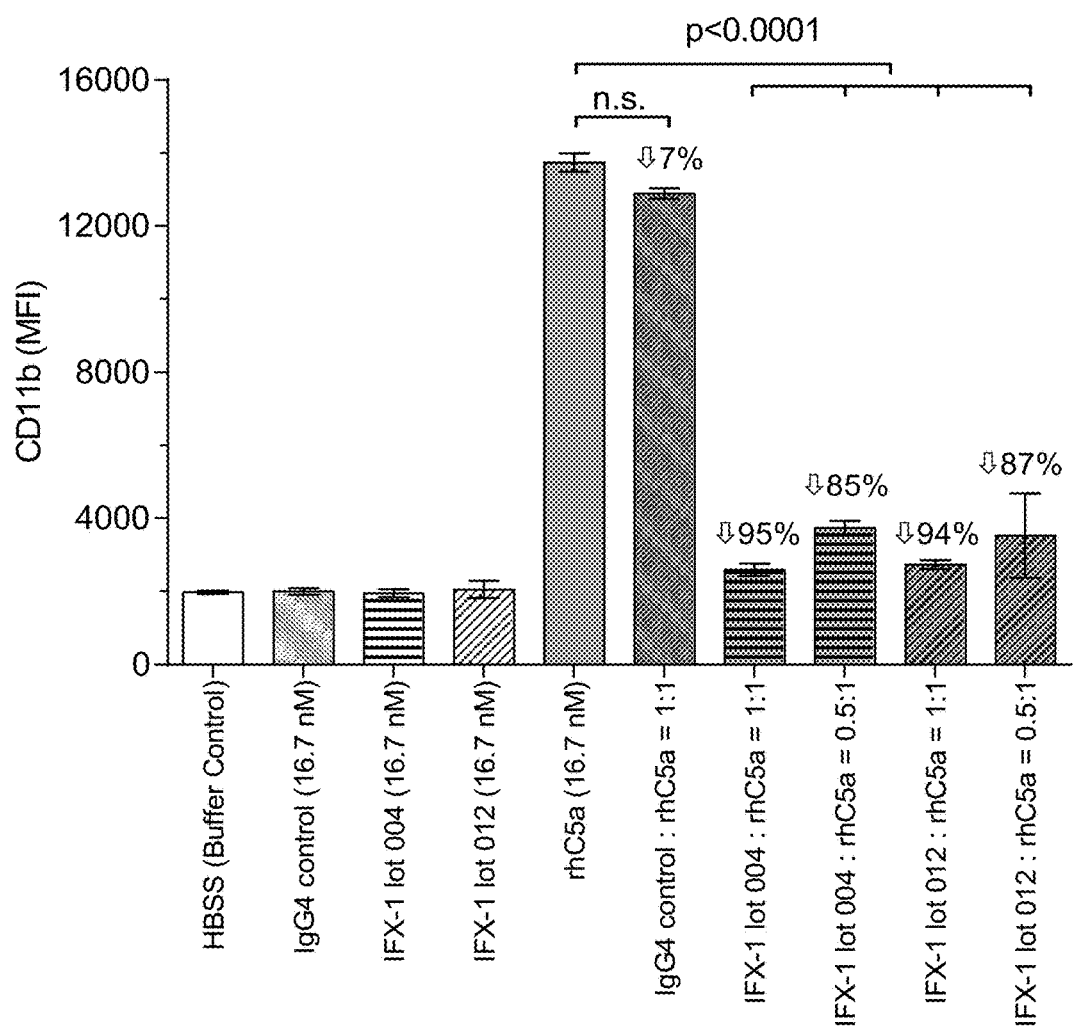
FIG. 1. Blocking activity of IFX-1 to recombinant human C5a (rhC5a)-induced CD11b upregulation on blood neutrophils. IFX-1-004 and IFX-1-012 represent two different production batches. Human whole blood was incubated with buffer, antibody alone, rhC5a alone, or combinations of different antibody concentration and rhC5a. After incubation, cells were stained with anti-mouse CD11b:FITC, and CD11b MFI was analyzed by flow cytometry. Results are presented as mean±SD. The percentage of IFX-1 blocking activity of C5a-induced CD11b expression is marked (arrow). Statistical differences were calculated by One-Way-ANOVA, p values of p<0.05 were statistically significant.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

Sequences: All sequences referred to herein are disclosed in the attached sequence listing that, with its whole content and disclosure, is a part of this specification.

In the context of the present invention, C5a particularly refers to human C5a. Human C5a is a 74 amino acid peptide with the following amino acid sequence:

```
                                           (SEQ ID NO: 1)
TLQKKIEEIA AKYKHSVVKK CCYDGACVNN DETCEQRAAR
ISLGPRCIKA FTECCVVASQ LRANISHKDM QLGR.
```

The amino acid sequence of human C5 can be found under the accession number UniProtKB P01031 (CO5_HUMAN).

As used herein, the term "inhibitor of C5a activity" refers to any compound that in any way reduces the activity of C5a. This activity reduction can be achieved by directly or indirectly lowering the concentration of C5a, or by reducing the activity of C5a, or by preventing that C5a exerts its effects on one or more of its receptors (e.g. on C5aR or C5L2), or by reducing the concentration or activity of one or more receptors of C5a.

In the context of the present invention, the expression "C5a receptor" refers to any potential C5a binding ligand on the cell surface, especially to any receptor protein to which C5a may bind and elicit a reaction on said receptor (e.g. activation or inhibition of the receptor). The term "C5a receptor" particularly encompasses the two receptors C5aR and C5L2. Alternative names for C5aR are C5aR1 and CD88. An alternative name for C5L2 is C5aR2.

In the context of the present invention, the expression "protein ligand" refers to any molecule composed of amino acids linked by peptide bonds, irrespective of the total size of the molecule, and that is capable of specifically binding to another molecule. Accordingly, the expression "protein ligand" comprises oligopeptides (≤100 amino acids) and polypeptides (>100 amino acids). The expression "protein ligand" also comprises cyclic peptides, irrespective of their size. The expression "protein ligand" particularly encompasses antibodies, antigen-binding fragments of antibodies, antibody-like proteins, and peptidomimetics.

As used herein, a first compound (e.g. a protein ligand or nucleic acid aptamer) is considered to "bind" to a second compound (e.g. a target protein), if it has a dissociation constant $K_d$ to said second compound of 1 mM or less, preferably 100 µM or less, preferably 50 µM or less, preferably 30 µM or less, preferably 20 µM or less, preferably 10 µM or less, preferably 5 µM or less, more preferably 1 µM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

The term "binding" according to the invention preferably relates to a specific binding. "Specific binding" means that a compound (e.g. a protein ligand or nucleic acid aptamer) binds stronger to a target such as an epitope for which it is specific compared to the binding to another target. A compound binds stronger to a first target compared to a second target, if it binds to the first target with a dissociation constant ($K_d$) which is lower than the dissociation constant for the second target. Preferably the dissociation constant ($K_d$) for the target to which the compound binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the compound does not bind specifically.

As used herein, the term "$K_d$" (usually measured in "mol/L", sometimes abbreviated as "M") is intended to refer to the dissociation equilibrium constant of the particular interaction between a compound (e.g. a protein ligand) and a target molecule.

Methods for determining binding affinities of compounds, i.e. for determining the dissociation constant $K_D$, are known to a person of ordinary skill in the art and can be selected for instance from the following methods known in the art: Surface Plasmon Resonance (SPR) based technology, Biolayer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Typically, the dissociation constant $K_D$ is determined at 20° C., 25° C., 30° C., or 37° C. If not specifically indicated otherwise, the $K_D$ values recited herein are determined at 20° C. by ELISA.

An "epitope", also known as antigenic determinant, is the part of a macromolecule that is recognized by the immune system, specifically by antibodies, B cells, or T cells. As used herein, an "epitope" is the part of a macromolecule capable of binding to a compound (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes can be distinguished in that the binding to the former but not the latter is lost in the presence of denaturing solvents.

A "paratope" is the part of an antibody that binds to the epitope. In the context of the present invention, a "paratope" is the part of a compound (e.g. a protein ligand) as described herein that binds to the epitope.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies, in particular of the antibodies described herein, e.g. antibodies expressed in prokaryotes, unglycosylated antibodies, antibodies expressed in eukaryotes (e.g. CHO cells), glycosylated antibodies, and any antigen-binding antibody fragments and derivatives as described below. Each heavy chain is comprised of a heavy chain variable region (abbreviated herein as VH or $V_H$) and a heavy chain constant region. Each light chain is comprised of a light chain variable region (abbreviated herein as VL or $V_L$) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those skilled in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1 (Heap C. J. et al. (2005) *Analysis of a 17-amino acid residue, virus-neutralizing microantibody*. J. Gen. Virol. 86:1791-1800). Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al., 2007 (Qiu X.-Q. et al. (2007) *Small antibody mimetics comprising two complementary-determining regions and a framework region for tumor targeting*. Nature biotechnology 25(8):921-929).

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen. Also comprised are immunoglobulin-like proteins that are selected through techniques including, for example, phage display to specifically bind to a target molecule or target epitope. The immunoglobulin molecules of the invention can be of any type (e.g., IgG, IgE, IgM, IgD, IgA and IgY), class (e.g., IgG1, IgG2, preferably IgG2a and IgG2b, IgG3, IgG4, IgA1 and IgA2) or subclass of immunoglobulin molecule.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen-binding site derived from another species, e.g. mouse. Moreover, antibodies of the invention include humanized molecules in which the antigen-binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as E. coli, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen-binding site that is substantially derived from an immunoglobulin from a non-human species, wherein the remaining immunoglobulin structure of the molecule is based upon the structure and/or sequence of a human immunoglobulin. The antigen-binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, Frontiers in Bioscience, 13:1619-1633, the content of which is herein incorporated by reference in its entirety. The review article by Almagro & Fransson is briefly summarized in US 2012/0231008 A1 which is the national stage entry of international patent application WO 2011/063980 A1. The contents of US 2012/0231008 A1 and WO 2011/063980 A1 are herein incorporated by reference in their entirety.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, F(ab')$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A.

90(14), 6444-6448), nanobodies (also known as single domain antibodies), anti-idiotypic (anti-Id) antibodies (including, e.g., anti-Id antibodies to antibodies described herein), and epitope-binding fragments of any of the above.

The antibodies described herein are preferably isolated. An "isolated antibody" as used herein, is intended to refer to an antibody which is substantially free of other antibodies having different antigenic specificities (e.g., an isolated antibody that specifically binds to C5a is substantially free of antibodies that specifically bind antigens other than C5a). An isolated antibody that specifically binds to an epitope, isoform or variant of human C5a may, however, have cross-reactivity to other related antigens, e.g. from other species (e.g. C5a species homologs, such as rat C5a). Moreover, an isolated antibody may be substantially free of other cellular material and/or chemicals. In one embodiment of the invention, a combination of "isolated" monoclonal antibodies relates to antibodies having different specificities and being combined in a well-defined composition.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, the term "nucleic acid aptamer" refers to a nucleic acid molecule that has been engineered through repeated rounds of in vitro selection or SELEX (systematic evolution of ligands by exponential enrichment) to bind to a target molecule (for a review see: Brody E. N. and Gold L. (2000), *Aptamers as therapeutic and diagnostic agents*. J. Biotechnol. 74(1):5-13). The nucleic acid aptamer may be a DNA or RNA molecule. The aptamers may contain modifications, e.g. modified nucleotides such as 2'-fluorine-substituted pyrimidines, and/or may comprise one or more nucleotides with L-ribose units (or L-deoxyribose) instead of the standard D-ribose units (or D-deoxyribose units).

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, affilins, affimers, affitins, alphabodies, anticalins, avimers, DARPins (designed ankyrin repeat proteins), fynomers, Kunitz domain peptides, and monobodies (for review see: Binz H. K. et al. (2005) *Engineering novel binding proteins from nonimmunoglobulin domains*. Nat. Biotechnol. 23 (10): 1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers" or as "antibody mimetics".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of non-natural amino acids).

In the context of the present invention, the term "small molecule" refers to a molecule with a molecular weight of 2 kDa or less, preferably with a molecular weight of 1 kDa or less. The term "small molecule" particularly refers to molecules that are neither oligopeptides nor oligonucleotides.

In the context of the present invention, the general expression "wherein A competes with B for binding to C", (e.g. in the expression "wherein said antibody or antigen-binding fragment thereof competes with one of the antibodies indicated under (a) for binding to C5a") is used to define the binding properties of the compound listed in position A. Said compound A binds to C and compound B also binds to C but compound A and compound B cannot bind to C at the same time; i.e. A and B bind to the same epitope (or at least to overlapping epitopes) on C. Such competition in binding can be determined by competitive ELISA or by Surface Plasmon Resonance (SPR) based technology or by any of the other techniques listed above in the context of the determination of binding affinities. If not explicitly stated otherwise, the competing binding properties of a compound are determined by ELISA at 20° C. using equimolar concentrations of the two competing compounds.

As used herein, a "cutaneous, neutrophilic, inflammatory disease" refers to any disease that is associated with an inflammation of the skin and with a neutrophilic infiltrate into the skin (e.g. into the epidermis) of an individual afflicted by said disease. The term "cutaneous, neutrophilic, inflammatory disease" particularly refers to hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); neutrophilic panniculitis; familial Mediterranean fever, cryopyrin-associated disorders, gout, and Schnitzler syndrome.

As used herein, the expression "HS-related disease" comprises without limitation Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); and subcorneal pustular dermatosis (SPD).

IFX-1 (alternative name: CaCP 29; InflaRx GmbH, Germany) is an antibody specifically binding to C5a. The CDR sequences and FR sequences of IFX-1 are disclosed in WO 2015/140304 A1 (in Table 3 on page 31), the content of which is hereby incorporated by reference in its entirety.

INab708 (InflaRx GmbH, Germany) is another antibody specifically binding to C5a. The CDR sequences and FR sequences of IFX-1 are also disclosed in WO 2015/140304 A1 (in Table 3 on page 31), the content of which is incorporated by reference in its entirety.

MEDI-7814 (MedImmune) is a recombinant humanized anti-C5a antibody. The crystal structure of the human C5a in complex with MEDI7814 is available in the RCSB Protein Data Bank under 4UU9 (DOI: 10.2210/pdb4uu9/pdb).

ALXN-1007 (Alexion) is a humanized anti-C5a antibody.

NOX-D21 (Noxxon) is a pegylated mixed L-RNA/DNA-aptamer (SPIEGELMER™) with the sequence 40 kDaPEG-aminohexyl-GCG AUG (dU)GG UGG UGA AGG GUU GUU GGG (dU)GU CGA CGC A(dC)G C (SEQ ID NO: 34). NOX-D21 targets C5a (Hyzewicz J, Tanihata J, Kuraoka M, Nitahara-Kasahara Y, Beylier T, Ruegg U T, Vater A, and Takeda S. 2017. *Low-Intensity Training and the C5a Complement Antagonist NOX-D21 Rescue the mdx Phenotype through Modulation of Inflammation.* Am. J. Pathol., 187(5): 1147-1161; electronically published ahead of print: Mar. 18, 2017).

Eculizumab (Alternative names: SOLIRIS™, 5G1-1; h5G1.1; Alexion Pharmaceuticals) is a recombinant humanized monoclonal IgG2/4;κ antibody produced by murine myeloma cell culture and purified by standard bioprocess technology. Eculizumab contains human constant regions from human IgG2 sequences and human IgG4 sequences and murine complementarity-determining regions grafted onto the human framework light- and heavy-chain variable regions. Eculizumab is composed of two 448 amino acid heavy chains and two 214 amino acid light chains and has a molecular weight of approximately 148 kDa. The heavy chain and light chain of eculizumab are disclosed, for example, in WO 2016/061066 A1 as SEQ ID NO: 1 and SEQ ID NO: 34, respectively. Nucleic acids that encode the heavy and light chains of eculizumab are disclosed, for example, in U.S. Pat. No. 6,355,245.

ALXN1210 (Alternative name: BNJ441; Alexion Pharmaceuticals) is an anti-C5 antibody. The heavy and light chains of ALXN1210 are disclosed in WO 2016/209956 A1 as SEQ ID NOs: 14 and 11, respectively.

ALXN5500 (Alexion) is a humanized anti-C5 antibody. It is a next-generation eculizumab candidate.

LFG316 (Alternative name: Tesidolumab, NOV-4; Morphosys, Novartis) is an anti-C5 antibody.

Figure 2:
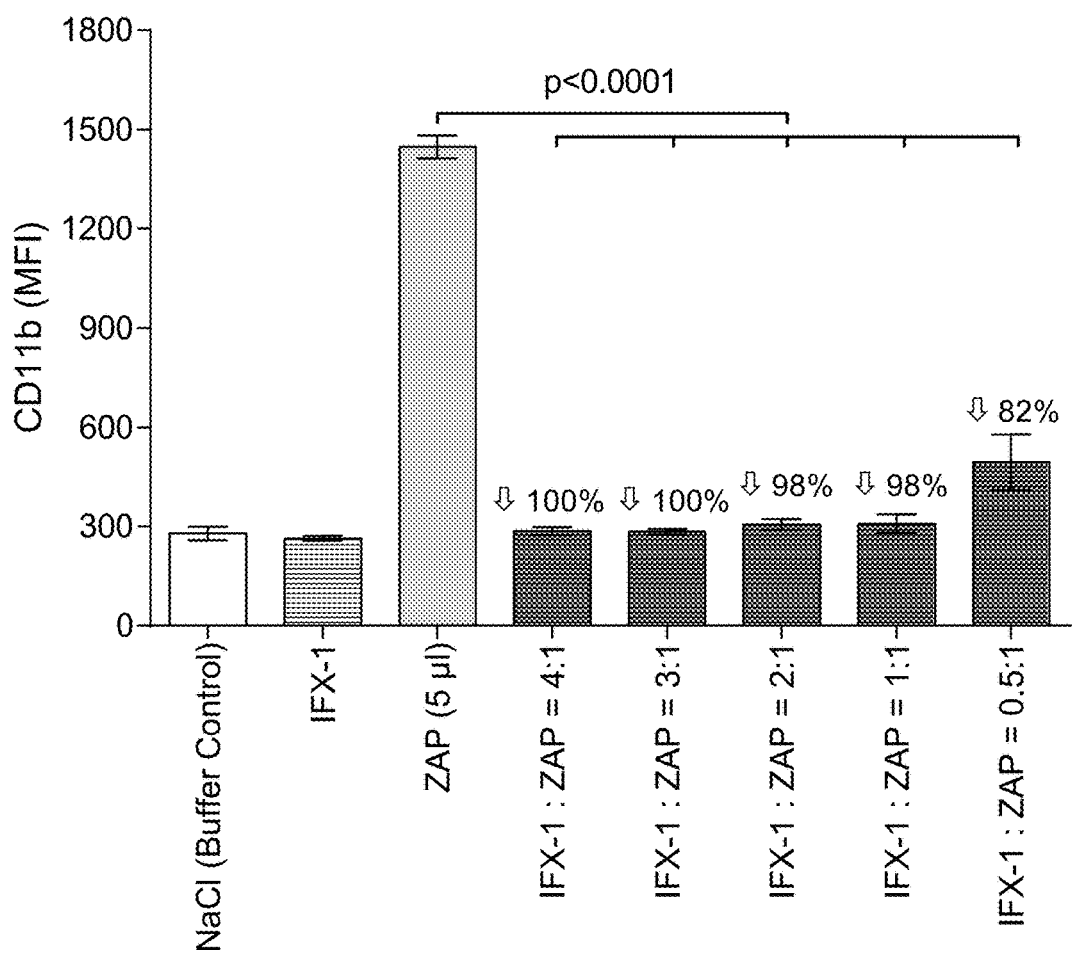
FIG. 2. Blocking activity of IFX-1 on endogenous C5a (eC5a)-driven CD11b upregulation on neutrophils. Zymosan-activated human plasma (ZAP) was used as the source of eC5a. Whole blood was incubated with buffer, IFX-1 alone, ZAP alone, or combinations of IFX-1 and ZAP. After incubation, cells were stained with anti-mouse CD11b:FITC and analyzed by flow cytometry. Results are presented as mean±SEM. The percentage of IFX-1 blocking activity of C5a-induced CD11b expression is marked (arrow). Statistical differences were calculated by One-Way-ANOVA, p values of p<0.05 were statistically significant.

COVERSIN™ (alternative names: EV 576; PAS-coversin; rEV 576; Tissue targeted COVERSIN™—Akari; Akari Therapeutics, Evolutec) is a recombinant protein molecule (16.7 kDa) derived from a salivary molecule from the *Ornithodros moubata* tick where it assists the parasite to feed without provoking a host immunological response. The amino acid sequence of the EV576 protein (i.e. COVERSIN) as well as its coding nucleotide sequence are shown in FIG. 2 of WO 2008/029167. COVERSIN™ binds to C5.

RA101495 (Ra Pharma) is a macrocyclic synthetic peptide inhibitor of C5 (Ricardo A, Arata M, DeMarco S, Dhamnaskar K, Hammer R, Fridkis-Hareli M, Rajagopal V, Seyb K, Tang G-Q, Tobe S and Treco D. 2015. *Preclinical Evaluation of RA101495, a Potent Cyclic Peptide Inhibitor of C5 for the Treatment of Paroxysmal Nocturnal Hemoglobinuria.* Blood 126:939).

ZIMURA® (Alternative names: Anti-C5 aptamer; ARC-187; ARC-1905; Avacincaptad pegol sodium; OphthoTech Corporation, Archemix Corporation) is a pegylated RNA aptamer that inhibits complement factor C5. The nucleotide sequence of ARC1905 (i.e. ZIMURA) is shown, for example, in WO 2005/079363 A2 as SEQ ID NO: 67, and its structure is shown in FIG. 22 of WO 2005/079363 A2.

AMY-201 (Amyndas Pharmaceuticals) is an engineered form of Factor H that directly links the regulatory and surface-recognition domains; Thus, it is a sort of mini-FH molecule.

Mirococept (alternative names: APT070 and APT 070C; originator: Adprotech; developer: Inflazyme Pharmaceuticals) consists of the first three short consensus domains of human complement receptor 1, manufactured in recombinant bacteria and modified with a membrane-targeting amphiphilic peptide based on the naturally occurring membrane-bound myristoyl-electrostatic switch peptide (Souza D G, Esser D, Bradford R, Vieira A T, and Teixeira M M. 2005. *APT070 (Mirococept), a membrane-localised complement inhibitor, inhibits inflammatory responses that follow intestinal ischaemia and reperfusion injury.* Br J Pharmacol 145(8): 1027-1034).

BikacioMab (Novelmed) is an F(ab)₂ fragment of an anti-factor Bb antibody termed NM001. Antibody NM001 is produced by hybridoma cell line 1D3 deposited under ATCC accession number PTA-8543.

Lampalizumab (alternative names: Anti-factor D Fab; FCFD4514S; RG7417; TNX-234; originator: Tanox, Developer: Genentech) is a humanized anti-Factor D Fab fragment that inhibits Factor D and the alternative complement pathway, through binding to an exosite on factor D.

ALN-CC5 (Alnylam) is an RNAi therapeutic targeting human, primate and rodent C5. Exemplary iRNA compositions targeting the C5 gene are described in WO 2016/044419.

Avacopan (also known by the name CCX168; Chemocentryx) is a small molecule (MW=581.66 g/mol) that has a structure according to formula I:

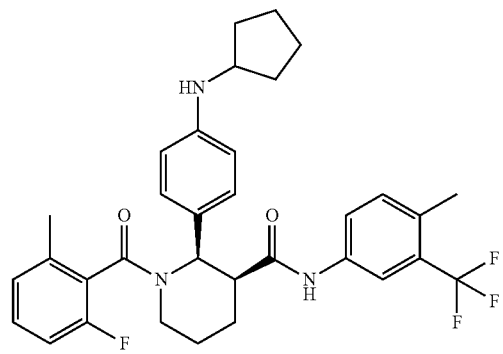

The IUPAC/Chemical name of avacopan is (2R,3S)-2-[4-(cyclopentylamino)phenyl]-1-(2-fluoro-6-methylbenzoyl)-N-[4-methyl-3-(trifluoromethyl)phenyl]piperidine-3-carboxamide. Avacopan is a selective inhibitor of C5aR. In the context of the present invention, the term "avacopan" refers to the compound according to formula I as well as to physiologically tolerable salts thereof.

As used herein, a "patient" means any mammal or bird who may benefit from a treatment with the compound described herein (i.e. with an inhibitor of C5a activity described herein). Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including chimpanzees and human beings. It is particularly preferred that the "patient" is a human being.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in subject.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Pharmaceutically acceptable" means approved by a regulatory agency of the Federal or a state government or listed in the U.S. Pharmacopeia or other generally recognized pharmacopeia for use in animals, and more particularly in humans.

Embodiments of the Invention

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to a compound for use in the treatment of a cutaneous, neutrophilic, inflammatory disease in a subject, wherein the compound is an inhibitor of C5a activity, and wherein the cutaneous, neutrophilic, inflammatory disease is selected from the group consisting of hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); neutrophilic panniculitis; familial Mediterranean fever, cryopyrin-associated disorders, gout, and Schnitzler syndrome.

In a second aspect, the present invention is directed to a method for the treatment of a cutaneous, neutrophilic, inflammatory disease in a subject, comprising the step of:
  administering to a subject in need thereof a therapeutic amount of a compound, wherein the compound is an inhibitor of C5a activity, and wherein the cutaneous, neutrophilic, inflammatory disease is selected from the group consisting of hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); neutrophilic panniculitis; familial Mediterranean fever, cryopyrin-associated disorders, gout, and Schnitzler syndrome.

In a third aspect, the present invention is directed to a use of a compound for the preparation of a pharmaceutical composition for the treatment of a cutaneous, neutrophilic, inflammatory disease, wherein the compound is an inhibitor of C5a activity, and wherein the cutaneous, neutrophilic, inflammatory disease is selected from the group consisting of hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); neutrophilic panniculitis; familial Mediterranean fever, cryopyrin-associated disorders, gout, and Schnitzler syndrome.

In some embodiments of any aspect of the present invention, the inhibitor of C5a activity:
  lowers the concentration of C5 (for example, by inhibiting formation and/or activity of C3 convertase; by inhibiting formation and/or activity of C5 convertase; by inhibiting the transcription of the C5 gene; by blocking translation of the C5 mRNA; by increasing degradation of the C5 mRNA; by increasing degradation of the C5 protein; or by prevention secretion of C5 from the liver);
  inhibits cleavage of C5 into C5a and C5b (for example, by inhibiting the C5 convertase or by binding to a cleavage site on C5 thereby blocking cleavage);
  lowers the concentration of C5a (for example, by increasing degradation of the C5a protein);
  inhibits binding between C5a and a C5a receptor (for example by binding to C5a or by binding to the C5a receptor);
  lowers the concentration of a C5a receptor (for example, by inhibiting transcription of a C5a receptor gene; by blocking translation of a C5a receptor mRNA; by increasing degradation of a C5a receptor mRNA; by increasing degradation of a C5a receptor protein); and/or
  inhibits the activity of a C5a receptor.

In some embodiments of any aspect of the present invention, the inhibitor of C5a activity is selected from the group consisting of a protein ligand (as defined above); an oligonucleotide; and a small molecule (as defined above). Oligonucleotides acting as inhibitors of C5a activity can achieve their inhibitory effect for example by binding to nucleic acid molecules (thereby inhibiting transcription and/or translation) or by binding to proteins (e.g. when the oligonucleotides are nucleic acid aptamers).

In some embodiments of any aspect of the present invention, the inhibitor of C5a activity is a protein ligand that specifically binds to C5 protein, or to C5a protein, or to a C5a receptor protein. In further embodiments, the protein ligand is selected from the group consisting of
(i) antibodies (e.g. anti-C5 antibodies, anti-C5a antibodies, anti-C5aR antibodies, or anti-C5L2 antibodies),
(ii) antigen-binding fragments of antibodies,
(iii) antibody-like proteins,
(iv) inhibitory variants of C5a,
(v) inhibitory variants of a C5a receptor (e.g. decoy receptors),
(vi) proteins acting on the complement pathway (e.g. Coversin); and
(vii) peptides (e.g., RA101495 (Ra Pharma, Cambridge, Mass.)).

In some embodiments of any aspect of the present invention, the inhibitor of C5a activity is a protein ligand or an oligonucleotide, preferably a protein ligand, that specifically binds to a conformational epitope formed by amino acid sequences NDETCEQRA (SEQ ID NO: 2) and SHKDMQL (SEQ ID NO: 3) of human C5a. Binding to the conformational formed by the amino acid sequences according to SEQ ID NOs: 2 and 3 means that the protein ligand or oligonucleotide binds to at least one amino acid within the amino acid sequence according to SEQ ID NO: 2 and to at least one amino acid within the amino acid sequence according to SEQ ID NO: 3. SEQ ID NO: 2 corresponds to amino acids 30-38 of human C5a. SEQ ID NO: 3 corresponds to amino acids 66-72 of human C5a.

In some embodiments of any aspect of the present invention the protein ligand or oligonucleotide, preferably the protein ligand, binds to at least one amino acid within the amino acid sequence according to DETCEQR (SEQ ID NO: 4). SEQ ID NO: 4 corresponds to amino acids 31-37 of human C5a.

In some embodiments of any aspect of the present invention the protein ligand or oligonucleotide, preferably the protein ligand, binds to at least one amino acid within the amino acid sequence according to HKDMQ (SEQ ID NO: 5), more preferably to at least one amino acid within the amino acid sequence KDM. SEQ ID NO: 5 corresponds to amino acids 67-71 of human C5a; the sequence KDM corresponds to amino acids 68-70 of human C5a.

In some embodiments of any aspect of the present invention the protein ligand or oligonucleotide, preferably the protein ligand, binds to at least one amino acid within the amino acid sequence DETCEQR (SEQ ID NO: 4) and to at least one amino acid within the amino acid sequence HKDMQ (SEQ ID NO: 5).

In some embodiments of any aspect of the present invention the protein ligand or oligonucleotide, preferably the protein ligand, binds to at least one amino acid within the amino acid sequence DETCEQR (SEQ ID NO: 4) and to at least one amino acid within the amino acid sequence KDM.

In some embodiments of any aspect of the present invention the two sequences forming the conformational epitope of C5a (e.g. sequence pairs according to SEQ ID NO: 2 and 3; SEQ ID NO: 4 and 5; or SEQ ID NO: 4 and sequence KDM) are separated by 1-50 contiguous amino acids that do not participate in binding to the binding moiety of the invention. In the following, such amino acids that do not participate in binding to the binding moiety of the invention will be referred to as "non-binding amino acids". The two sequences forming the conformational epitope are preferably separated by 6-45 contiguous non-binding amino acids, more preferably by 12-40 contiguous non-binding amino acids, more preferably by 18-35 contiguous non-binding amino acids, more preferably by 24-30 contiguous non-binding amino acids, more preferably by 25-29 contiguous non-binding amino acids, even more preferably by 26-28 contiguous non-binding amino acids, and most preferably by 27 contiguous non-binding amino acids.

In some embodiments of any aspect of the present invention the protein ligand or oligonucleotide, preferably the protein ligand, specifically binding to a conformational epitope of C5a has a binding constant to human C5a with a $K_d$ value of 10 nM or less, preferably 9 nM or less, more preferably 8 nM or less, more preferably 7 nM or less, more preferably 6 nM or less, more preferably 5 nM or less, more preferably 4 nM or less, more preferably 3 nM or less, more preferably 2 nM or less, and even more preferably 1 nM or less. In some embodiments of any aspect of the present invention the dissociation constant $K_d$ between the binding moiety and human C5a is between 1 pM (picomolar) and 5 nM (nanomolar), more preferably between 2 pM and 4 nM, more preferably between 5 pM and 3 nM, more preferably between 10 pM and 2 nM, more preferably between 50 pM and 1 nM, more preferably between 100 pM and 900 pM, more preferably between 200 pM and 800 pM, more preferably between 300 pM and 700 pM, and even more preferably between 400 pM and 600 pM.

In some embodiments of any aspect of the present invention the protein ligand or oligonucleotide, preferably the protein ligand, specifically binding to C5a exhibits at least 75% blocking activity, preferably at least 80% blocking activity, more preferably at least 85% blocking activity, more preferably at least 90% blocking activity, more preferably at least 95% blocking activity for biological effects induced by one molecule C5a, particularly human C5a. These particular blocking activities refer to those embodiments, wherein the binding moiety comprises a single paratope binding to C5a, preferably human C5a. In embodiments, wherein the binding moiety comprises two or more C5a-specific paratopes, said blocking activities of at least 75%, preferably at least 80%, more preferably at least 85%, etc. are achieved when one binding-moiety molecule is contacted with a number of C5a molecules equal to the number of C5a-specific paratopes present in the binding moiety. In other words, when the paratopes of a binding moiety described herein and C5a are present in equimolar concentrations, the binding moiety exhibits at least 75% blocking activity, preferably at least 80% blocking activity, more preferably at least 85% blocking activity, more preferably at least 90% blocking activity, and more preferably at least 95% blocking activity for biological effects induced by C5a. A preferred biological effect to be blocked is C5a-induced lysozyme release from human whole blood cells. Assays for determining this C5a-induced lysozyme release and its blocking are described, for example, in WO 2011/063980 A1.

In some embodiments of any aspect of the present invention the protein ligand is an antibody or an antigen-binding fragment thereof, wherein said antibody or antigen-binding fragment thereof comprises
(i) a heavy chain CDR3 sequence as set forth in SEQ ID NO: 6; or
(ii) a heavy chain CDR3 sequence as set forth in SEQ ID NO: 7;
wherein the heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In some embodiments of any aspect of the present invention the protein ligand is an antibody or an antigen-binding fragment thereof, wherein said antibody or antigen-binding fragment thereof comprises
(iii) a light chain CDR3 sequence as set forth in SEQ ID NO: 8; or
(iv) a light chain CDR3 sequence as set forth in SEQ ID NO: 9;
wherein the light chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In some embodiments of any aspect of the present invention the protein ligand is an antibody or an antigen-binding fragment thereof, wherein said antibody or antigen-binding fragment thereof comprises
(i) a heavy chain CDR3 sequence as set forth in SEQ ID NO: 6 and a light chain CDR3 sequence as set forth in SEQ ID NO: 8; or
(ii) a heavy chain CDR3 sequence as set forth in SEQ ID NO: 7 and a light chain CDR3 sequence as set forth in SEQ ID NO: 9;
wherein the heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions; and
wherein the light chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In some embodiments of any aspect of the present invention the protein ligand is an antibody or an antigen-binding fragment thereof, wherein said antibody or antigen-binding fragment thereof comprises at least one of the following sequences:

(v) a heavy chain CDR2 sequence according to SEQ ID NO: 10;
(vi) a heavy chain CDR2 sequence according to SEQ ID NO: 11;
(vii) a light chain CDR2 sequence according to SEQ ID NO: 12;
(viii) a light chain CDR2 sequence according to SEQ ID NO: 13;
(ix) a heavy chain CDR1 sequence according to SEQ ID NO: 14;
(x) a heavy chain CDR1 sequence according to SEQ ID NO: 15;
(xi) a light chain CDR1 sequence according to SEQ ID NO: 16; or
(xii) a light chain CDR1 sequence according to SEQ ID NO: 17;
wherein the heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions;
wherein the light chain CDR2 sequence optionally comprises 1, 2, or 3 amino acid exchanges, preferably conservative amino acid exchanges, 1, 2, or 3 amino acid deletions, and/or 1, 2, or 3 amino acid additions;
wherein the heavy chain CDR1 sequence optionally comprises 1, 2 or 3 amino acid exchanges, preferably conservative amino acid exchanges, 1, 2, or 3 amino acid deletions, and/or 1, 2, or 3 amino acid additions; and
wherein the light chain CDR1 sequence optionally comprises 1, 2, or 3 amino acid exchanges, preferably conservative amino acid exchanges, 1, 2, or 3 amino acid deletions, and/or 1, 2, or 3 amino acid additions.

In particular embodiments, the total number of these optional changes recited above in each one of the amino acid sequences according to SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, and SEQ ID NO: 17, i.e. the total number of exchanges, deletions and additions in each sequence, is 1 or 2.

In particular embodiments the total number of exchanges, deletions, and additions added up for all CDRs present in an antibody or antigen-binding fragment thereof is between 1 and 5 (e.g. 1, 2, 3, 4, or 5).

In some embodiments of any aspect of the present invention the protein ligand is an antibody or an antigen-binding fragment thereof, comprises one of the sets of heavy chain CDR3, heavy chain CDR2, and heavy chain CDR1 sequences as listed below in Table 1,
wherein each heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions;
wherein each heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions; and
wherein each heavy chain CDR1 sequence optionally comprises 1, 2, or 3 amino acid exchanges, preferably conservative amino acid exchanges, 1, 2, or 3 amino acid deletions, and/or 1, 2, or 3 amino acid additions:

TABLE 1

Sets of heavy chain CDR sequences suitable for use in the antibodies or fragments thereof of the present invention

| Symbol of heavy chain set | CDR3 sequence | CDR2 sequence | CDR1 sequence |
|---|---|---|---|
| A | SEQ ID NO: 6 | SEQ ID NO: 10 | SEQ ID NO: 14 |
| B | SEQ ID NO: 6 | SEQ ID NO: 10 | SEQ ID NO: 15 |
| C | SEQ ID NO: 6 | SEQ ID NO: 11 | SEQ ID NO: 14 |
| D | SEQ ID NO: 6 | SEQ ID NO: 11 | SEQ ID NO: 15 |
| E | SEQ ID NO: 7 | SEQ ID NO: 10 | SEQ ID NO: 14 |
| F | SEQ ID NO: 7 | SEQ ID NO: 10 | SEQ ID NO: 15 |
| G | SEQ ID NO: 7 | SEQ ID NO: 11 | SEQ ID NO: 14 |
| H | SEQ ID NO: 7 | SEQ ID NO: 11 | SEQ ID NO: 15 |

I In some embodiments of any aspect of the present invention the protein ligand is an antibody or an antigen-binding fragment thereof, comprises one of the following sets of light chain CDR3, light chain CDR2, and light chain CDR1 sequences as listed in Table 2,
wherein each light chain CDR3 sequence optionally comprises 1, 2, or 3 amino acid exchanges, preferably conservative amino acid exchanges, 1, 2, or 3 amino acid deletions, and/or 1, 2, or 3 amino acid additions;
wherein each light chain CDR2 sequence optionally comprises 1, 2, or 3 amino acid exchanges, preferably conservative amino acid exchanges, 1, 2, or 3 amino acid deletions, and/or 1, 2, or 3 amino acid additions; and
wherein each light chain CDR1 sequence optionally comprises 1, 2, or 3 amino acid exchanges, preferably conservative amino acid exchanges, 1, 2, or 3 amino acid deletions, and/or 1, 2, or 3 amino acid additions:

TABLE 2

Sets of light chain CDR sequences suitable for use in the antibodies or fragment thereof of the present invention
Since the CDR2 light chain sequence of antibody IFX-1 (SEQ ID NO: 12) is identical to the CDR2 light chain sequence of antibody INab708 (SEQ ID NO: 13), sets including SEQ ID NO: 13 would be redundant to sets including SEQ ID NO: 12. Therefore, the table only list four sets of light chain CDR sequences.

| Number of light chain set | CDR3 sequence | CDR2 sequence | CDR1 sequence |
|---|---|---|---|
| I | SEQ ID NO: 8 | SEQ ID NO: 12 | SEQ ID NO: 16 |
| II | SEQ ID NO: 8 | SEQ ID NO: 12 | SEQ ID NO: 17 |
| III | SEQ ID NO: 9 | SEQ ID NO: 12 | SEQ ID NO: 16 |
| IV | SEQ ID NO: 9 | SEQ ID NO: 12 | SEQ ID NO: 17 |

In some embodiments of any aspect of the present invention the protein ligand is an antibody or an antigen-binding fragment thereof, comprises one of the heavy CDR sets A-H listed above in Table 1 and one of the light chain CDR sets I-IV listed above in Table 2, i.e. one of the following combinations of sets: A-I, A-II, A-III, A-IV, B-I, B-II, B-IV, C-I, C-II, C-III, C-IV, D-I, D-II, D-IV, E-I, E-II, E-IV, F-I, F-II, F-IV, G-I, G-II, G-IV, H-I, H-II, H-III, or H-IV (wherein the combinations A-I and H-IV are especially preferred), wherein each heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions; wherein each heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions;
wherein each heavy chain CDR1 sequence optionally comprises 1, 2, or 3 amino acid exchanges, preferably conservative amino acid exchanges, 1, 2, or 3 amino acid deletions and/or 1, 2, or 3 amino acid additions;
wherein each light chain CDR3 sequence optionally comprises 1, 2, or 3 amino acid exchanges, in particular conservative amino acid exchanges, 1, 2, or 3 amino acid deletions, and/or 1, 2, or 3 amino acid additions;
wherein each light chain CDR2 sequence optionally comprises 1, 2, or 3 amino acid exchanges, preferably conservative amino acid exchanges, 1, 2, or 3 amino acid deletions, and/or 1, 2, or 3 amino acid additions; and
wherein each light chain CDR1 sequence optionally comprises 1, 2, or 3 amino acid exchanges, preferably conservative amino acid exchanges, 1, 2, or 3 amino acid deletions and/or 1, 2, or 3 amino acid additions.

In some embodiments of any aspect of the present invention the protein ligand is an antibody or an antigen-binding fragment thereof, comprises a VH domain that comprises, essentially consists of or consists of (i) the VH domain of IFX-1 or (ii) the VH domain of INab708.

The FR1, CDR1, FR2, CDR2, FR3, CDR3, and FR4 sequences defining the VH domains of IFX-1 and INab708 are shown below in Table 3.

In some embodiments of any aspect of the present invention the protein ligand is an antibody or an antigen-binding fragment thereof, comprises a VL domain that comprises, essentially consists of or consists of (i) the VL domain of IFX-1 or (ii) the VL domain of INab708.

The FR1, CDR1, FR2, CDR2, FR3, CDR3, and FR4 sequences defining the VL domains of IFX-1 and INab708 are shown below in Table 3.

TABLE 3

CDR and FR sequences of antibodies IFX-1 and INab708 (Chothia classification mode)

| IFX-1: | INab708: |
|---|---|
| Heavy Chain: | Heavy Chain: |
| FR1: QVQLQQSGPQLVRPGTSVKIS (= SEQ ID NO: 18) | FR1: VQLLESGAELMKPGASVKIS (SEQ ID NO: 26) |
| CDR1: CKASGYSFTTFWMD (= SEQ ID NO: 14) | CDR1: CKATGNTFSGYWIE (= SEQ ID NO: 15) |
| FR2: WVKQRPGQGLEWIGR (SEQ ID NO: 19) | FR2: WVKQRPGHGLEWIGE (SEQ ID NO: 27) |
| CDR2: IDPSDSESRLDQ (= SEQ ID NO: 10) | CDR2: ILPGSGSTNYNE (= SEQ ID NO: 11) |
| FR3: RFKDRATLTVDKSSSTVYMQLSSPTSEDSAVYY (SEQ ID NO: 20) | FR3: KFKGKATLTADTSSNTAYMQLSSLTSEDSAVYY (SEQ ID NO: 28) |
| CDR3: CARGNDGYYGFAY (= SEQ ID NO: 6) | CDR3: CTRRGLYDGSSYFAY (= SEQ ID NO: 7) |
| FR4: WGQGTLVTVSS (SEQ ID NO: 21) | FR4: WGQGTLVTVSA (SEQ ID NO: 29) |
| Light chain: | Light Chain: |
| FR1: DIVLTQSPASLAVSLGQRATIS (SEQ ID NO: 22) | FR1: DIVLTQSPASLAVSLGQRATIS (SEQ ID NO: 30) |
| CDR1: CKASQSVDYDGDSYMK (= SEQ ID NO: 16) | CDR1: CKASQSVDYDGDSYMN (= SEQ ID NO: 17) |
| FR2: WYQQKPGQPPKLL (SEQ ID NO: 23) | FR2: WYQQKPGQPPKLL (SEQ ID NO: 31) |
| CDR2: IYAASNL (= SEQ ID NO: 12) | CDR2: IYAASNL (= SEQ ID NO: 13) |
| FR3: QSGIPARFSGSGSGTDFTLNIHPVEEEDAATYY (SEQ ID NO: 24) | FR3: GSGIPARFSGSGSGTDFTLNIHPVEEEVAATYY (SEQ ID NO: 32) |
| CDR3: CQQSNEDPYT (= SEQ ID NO: 8) | CDR3: CQQNNEDPLT (= SEQ ID NO: 9) |
| FR4: FGGGTKLEIK (SEQ ID NO: 25) | FR4: FGAGTLLELK (SEQ ID NO: 33) |

In some embodiments of any aspect of the present invention, the inhibitor of C5a activity is an oligonucleotide that specifically binds to C5, or to C5a, or to a C5a receptor. In further embodiments, the oligonucleotide is a nucleic acid aptamer. The nucleic acid aptamer may be selected from the group consisting of DNA-aptamers, D-RNA aptamers, and L-RNA aptamers (e.g., SPIEGELMERS™).

In some embodiments of any aspect of the present invention, the inhibitor of C5a activity reduces expression of C5 protein or C5a receptor protein. In further embodiments, said inhibitor of C5a activity that reduces expression of C5 protein or C5a receptor protein is an oligonucleotide selected from the group consisting of antisense DNA, antisense RNA, siRNA, and miRNA.

In some embodiments of any aspect of the present invention, the C5a receptor is selected from the group consisting of C5aR and C5L2. In preferred embodiments of any aspect of the present invention, the C5a receptor is C5aR (also known as CD88 or C5aR1).

In some embodiments of any aspect of the present invention, the inhibitor of C5a activity is selected from the group consisting of:
(a) IFX-1, INab708, MEDI-7814, ALXN-1007, or NOX-D21, or an antigen-binding fragment thereof;
(b) an antibody or an antigen-binding fragment thereof, wherein said antibody or antigen-binding fragment thereof competes with one of the antibodies indicated under (a) for binding to C5a;
(c) Eculizumab, ALXN1210, ALXN5500, or LFG316, or an antigen-binding fragment thereof;
(d) an antibody or an antigen-binding fragment thereof, wherein said antibody or antigen-binding fragment thereof competes with one of the antibodies indicated under (c) for binding to C5;
(e) Coversin or RA101495;
(f) an antibody or an antigen-binding fragment thereof or protein or macrocyclic peptide wherein said antibody or antigen-binding fragment thereof or macrocyclic peptide competes with one of the or protein or peptides indicated under (e) for binding to C5;
(g) Zimura;
(h) an antibody or an antigen-binding fragment thereof or an aptamer, wherein said antibody or antigen-binding fragment thereof or aptamer competes with Zimura for binding to C5;
(i) AMY-201 or Mirococept;
(j) an antibody or an antigen-binding fragment thereof or a protein wherein said antibody or antigen-binding fragment thereof or protein competes with one of the proteins indicated under (i) for binding to C3b;
(k) Bikaciomab;
(l) an antibody or an antigen-binding fragment thereof, wherein said antibody or antigen-binding fragment thereof competes with Bikaciomab for binding to Factor B;
(m) Lampalizumab;
(n) an antibody or an antigen-binding fragment thereof, wherein said antibody or antigen-binding fragment thereof competes with Lampalizumab for binding to Factor D;
(o) ALN-CC5; and
(p) Avacopan.

In some embodiments of any aspect of the present invention, the cutaneous, neutrophilic, inflammatory disease is an auto-inflammatory disease (more precisely: a cutaneous, neutrophilic, auto-inflammatory disease); or an autoimmune disease with cutaneous inflammation (more precisely: an autoimmune disease with cutaneous, neutrophilic inflammation).

In some embodiments of any aspect of the present invention, the cutaneous, neutrophilic, inflammatory disease is an auto-inflammatory disease selected from the group consisting of hidradenitis suppurativa (HS); Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); subcorneal pustular dermatosis (SPD); epidermolysis bullosa acquisita, erythema elevatum diutinum (EED); and neutrophilic panniculitis.

In some embodiments of any aspect of the present invention, the cutaneous, neutrophilic, inflammatory disease is HS or a HS-related disease selected from the group consisting of Pyoderma gangrenosum (PG); PAPA (pyogenic arthritis, PG and acne); PASH (PG, acne and hidradenitis suppurativa); PAPASH (pyogenic arthritis, acne, PG and hidradenitis suppurativa); Sweet syndrome (SS); and subcorneal pustular dermatosis (SPD).

In some embodiments of any aspect of the present invention, the cutaneous, neutrophilic, inflammatory disease is an autoimmune disease with cutaneous inflammation selected from the group consisting of familial Mediterranean fever, cryopyrin-associated disorders, gout, and Schnitzler syndrome.

In some embodiments of the first or third aspect of the present invention, the compound is to be administered at a dose of 800 mg once per week or at a dose of 800 mg twice per week. In further embodiments of the first or third aspect,
the inhibitor of C5a activity is a compound specifically binding to C5a (preferably selected from the group consisting of IFX-1, INab708, MEDI-7814, ALXN-1007, NOX-D21, and an antigen-binding fragment thereof; more preferably the inhibitor of C5a activity is selected from the group consisting of IFX-1, INab708, MEDI-7814, ALXN-1007 and an antigen-binding fragment thereof; even more preferably, the inhibitor of C5a activity is selected from the group consisting of IFX-1 and an antigen-binding fragment thereof; most preferably the inhibitor of C5a activity is IFX-1); and
the cutaneous, neutrophilic, inflammatory disease is hidradenitis suppurativa (HS); and
the compound is to be administered at a dose of 800 mg once per week or at a dose of 800 mg twice per week.

In further embodiments of the first or third aspect, the inhibitor of C5a activity is to be administered intravenously. In further embodiments of the first or third aspect, the inhibitor of C5a activity is to be administered twice per week at a dose of 800 mg in the first week of treatment and once per week at a dose of 800 mg in the second and subsequent weeks of treatment. In further embodiments of the first or third aspect, the total duration of treatment is between 5 and 12 weeks (e.g. 5 weeks, 6, weeks, 7 weeks, 8 weeks, 9 weeks, 10 weeks, 11 weeks, or 12 weeks).

In some embodiments of the second aspect of the present invention, the compound is administered at a dose of 800 mg once per week or at a dose of 800 mg twice per week. In further embodiments of the second aspect,
the inhibitor of C5a activity is a compound specifically binding to C5a (preferably selected from the group consisting of IFX-1, INab708, MEDI-7814, ALXN-1007, NOX-D21, and an antigen-binding fragment thereof; more preferably the inhibitor of C5a activity is selected from the group consisting of IFX-1, INab708, MEDI-7814, ALXN-1007 and an antigen-binding fragment thereof; even more preferably, the inhibitor of C5a activity is selected from the group consisting of IFX-1 and an antigen-binding fragment thereof; most preferably the inhibitor of C5a activity is IFX-1); and
the cutaneous, neutrophilic, inflammatory disease is hidradenitis suppurativa (HS); and
the compound is administered at a dose of 800 mg once per week or at a dose of 800 mg twice per week.

In further embodiments of the second aspect, the inhibitor of C5a activity is administered intravenously. In further embodiments of the second aspect, the compound is administered twice per week at a dose of 800 mg in the first week of treatment and once per week at a dose of 800 mg in the second and subsequent weeks of treatment. In further embodiments of the second aspect, the total duration of treatment is between 5 and 10 weeks (e.g. 5 weeks, 6, weeks, 7 weeks, 8 weeks, 9 weeks, 10 weeks, 11 weeks, or 12 weeks).

Pharmaceutical Compositions and Modes of Administration

In the practice of any aspect of the present invention, a compound (e.g. an inhibitor of C5a activity described herein) or a pharmaceutical composition comprising the compound may be administered to a patient by any route established in the art which provides a sufficient level of the compound in the patient. It can be administered systemically or locally. Such administration may be parenterally, transmucosally, e.g., orally, nasally, rectally, intravaginally, sublingually, submucosally, transdermally, or by inhalation. Preferably, administration is parenteral, e.g., via intravenous or intraperitoneal injection, and also including, but is not limited to, intra-arterial, intramuscular, intradermal and subcutaneous administration. If the compound described herein (e.g. an inhibitor of C5a activity described herein) or a pharmaceutical composition comprising the compound is administered locally, it can be injected directly into the organ or tissue to be treated.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. Pharmaceutical compositions may also be administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, a compound described herein (e.g. an inhibitor of C5a activity described herein) is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, for example, a compound (e.g. an inhibitor of C5a activity described herein) or a pharmaceutical composition comprising the compound can be delivered in a controlled-release system. For example, the compound may be administered using intravenous infusion, an implantable osmotic pump, a transdermal patch, liposomes, or other modes of administration. In one embodiment, a pump may be used (see Sefton (1987) *CRC Crit. Ref. Biomed. Eng.* 14: 201; Buchwald et al. (1980) *Surgery* 88:507; Saudek et al. (1989) *N. Eng. J. Med.* 321: 574). In another embodiment, the compound can be delivered in a vesicle, in particular a liposome (see Langer (1990) *Science* 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) *J. Macromol. Sci. Rev. Macromol. Chem.* 23: 61; see also Levy et al. (1985) *Science* 228:190; During et al. (1989) *Ann. Neurol.* 25: 351; Howard et al. (1989) *J. Neurosurg.* 71: 105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990, *Science* 249: 1527-1533).

In a specific embodiment, it may be desirable to administer a compound described herein (e.g. an inhibitor of C5a activity described herein) or a pharmaceutical composition comprising the compound locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of the pharmaceutical composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be prevented and or treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

EXAMPLES

The following Examples are provided for further illustration of the invention. The invention, however, is not limited thereto, and the following Examples merely show the practicability of the invention on the basis of the above description.

1. Methods 1.1 Preparation of Zymosan A Stock Solution and Activated Plasma

Zymosan A was dissolved to 2 mg/ml in 50 ml sterile saline and boiled for 1 h at 100° C. After centrifugation, supernatant was discarded and the pellet was resuspended in 50 ml sterile saline. After a second centrifugation step, pellet was resuspended in 5 ml sterile saline to obtain a 20 mg/ml stock solution. Stock solution was aliquoted and stored at −20° C. until use. To activate the plasma, zymosan A stock solution and 100 µl plasma were mixed and incubated at 37° C. for ~30 min. After incubation, tubes were centrifuged and the supernatant was aliquoted and stored at −20° C. until use.

1.2 CD11b Assay Using rhC5a or ZAP as Stimulants

Human whole blood was stimulated with rhC5a or ZAP. To test blocking activity of IFX-1 and control IgG4 on rhC5a, the antibodies were diluted to final Ab/Ag ratios of 1:1 and 0.5:1. To test the blocking activity of IFX-1 on eC5a, IFX-1 was diluted to reach final Ab/Ag molar ratios of approximately 4:1/3:1/2:1/1:1/0.5:1. Blood only with buffer served as a non-stimulation control to assess baseline CD11b expression. Antibody alone was used to determine the effects of the antibody on non-stimulated human blood. The complete mixture (Ab/Ag/blood) was incubated at 37° C. for 20 min to stimulate C5a-induced up-regulation of CD11b, and anti-mouse CD11b:FITC were added and samples were incubated for 30 min on ice to minimize background staining. Granulocytes were gated and mean fluorescence intensity (MFI) of FITC labeled (CD11b expressing) granulocytes was examined by Flow Cytometer.

1.3 CD11b Assay Using rhC5a or Zymosan A in the Whole Blood

Human blood was stimulated with rhC5a or zymosan A, and the complete mixture (Ab/Ag/blood) was incubated at 37° C. for 20 min to stimulate C5a-induced up-regulation of CD11b. After incubation, 2 µl of anti-mouse CD11b:FITC or isotype control were added and samples were incubated for 30 min on ice to minimize background staining. After lysis, cells were analyzed using the flow cytometer. On the FSC/SSC, granulocytes were gated and mean fluorescence intensity (MFI) of FITC labeled (CD11b expressing) granulocytes was examined for the whole sample set.

1.4 Cytokine IL-8 ELISA

Human IL-8 ELISA was performed as recommended in the instruction manual under section "Assay procedure" (eBioscience Inc., San Diego, Calif.). Briefly, coating was performed overnight at 4° C. using 100 µl 1× capture antibody. Plates were blocked using 200 µl 1× assay diluents at RT for 1 h. Standard stock solutions were diluted with 1× assay diluents to the desired concentration, followed by 6 serial 1:2 dilutions. Sample supernatants were diluted as required in 1× assay diluents. According to the "Assay procedure", 100 µl of standard dilutions and sample dilutions were added to the coated plate and incubated at RT for 1 h, followed by the incubation with 100 µl 1× detection antibody (RT, 1 h) and 100 µl 1× avidin-HRP (RT, 30 min). Color development was performed with 100 µl TMB substrate solution at RT for 10 min in the dark and was stopped with 100 µl stop solution. Absorbance was read out within 30 min using the plate reader at 450 nm. Zero standard value (blank) was subtracted from all standards and samples. Cytokine concentration of samples was calculated using a log(x)/log(y) standard curve of included standard samples.

1.5 C5a ELISA

Capture antibody, a purified anti-human C5a monoclonal antibody (InflaRx GmbH, Jena, Germany), was coated overnight with a final concentration of 0.5 μg/mL on the ELISA plate. After blocking, calibration samples (recombinant human C5a, Sigma, Taufkirchen, Germany) and samples diluted in assay diluent (1×PBS, 0.05% Tween20, 2% heat-inactivated FBS) were incubated for 90 minutes at room temperature. Mouse anti-human C5/C5a antibody clone 561 (Hycult Biotech, Uden, The Netherlands) diluted to 2 μg/mL in assay diluent was applied as the primary detection antibody for a 60-minute incubation step at room temperature, followed by 30-minute incubation with a secondary horseradish peroxidase labeled antibody (goat anti-mouse IgG2a polyclonal antibody, SouthernBiotech, Birmingham, USA) diluted to 0.05 μg/mL in assay diluent. Color development was performed with tetramethylbenzidine substrate solution (TMB, Biozol, Eching, Germany) and was stopped with 3.7 N sulfuric acid. The OD was read at an absorbance of 450 nm by Tecan INFINITE® 200 reader and Tecan MAGELLAN™ (Tecan Group, Maennedorf, Switzerland). The in-house developed C5a ELISA was validated according to the EMA guideline on bioanalytical method validation.

Intra-assay and inter-assay precision tested with five different concentrations showed a coefficient of variance (CV) of 0.65% to 4.96% and 1.50% to 4.88% for six and 18 repetitions, respectively. Recovery analysis of spiked recombinant human C5a in buffer resulted in recoveries of 86.98±1.20% (mean±SD) at the lower limit of quantification and 91.50±3.29% at the upper limit of quantification. No cross-reactivity for C3, C3a and C4 and cross-reactivity of <0.01% for C5b-6 was detected. Human IgG4 antibodies did not interfere with the assay. C5a levels from 20 human volunteers in citrate plasma resulting in 17.08 ng/ml±6.96 ng/ml with a range of 7.52 ng/mL to 30.17 ng/mL. No difference was identified for the measurements of C5a and C5a-desArg by using this ELISA.

1.6 Measurements of Complement Activation Products

Concentrations of complement activation products C3a, C5a and membrane attack complex C5b-9 were measured by ELISA method. C3a ELISA (BD OptEIA™ Human C3a ELISA Kit, BD Bioscience, Germany) was conducted according to the manufacturer instruction. C5b-9 concentration was determined using the C5b-9 ELISA validated by InflaRx based on the BD OptEIA™ Human C5b-9 ELISA Set (BD Bioscience). C5a concentration was measured using one C5a ELISA established and validated by InflaRx described above.

1.7 Statistical Analysis

All results were expressed as the mean±standard deviation. Statistical differences between groups, after baseline correction, were calculated by One-Way-ANOVA, including Tukey's multiple comparison test or by the students t-test for two groups. The p value of 0.05 was used in the calculation to determine whether there were any significant differences between any two groups. Creating of graphs and statistical analysis were performed with GraphPad PRISM® V6.05 (CA, USA).

2. Preclinical Relevant Data

2.1 C5a Activation of Neutrophils and the Blocking Effect of IFX-1

As CD11b up-regulation is a hallmark and a sensitive marker for neutrophil activation, CD11b levels on neutrophils were employed to evaluate the neutrophil activation. The human whole blood model was used to assess the blocking activity of IFX-1 to recombinant human C5a in this study. Human whole blood was incubated with buffer, antibody alone, rhC5a alone, or combinations of different antibody concentration and rhC5a. After incubation, cells were stained with anti-mouse CD11b:FITC, and CD11b MFI was analyzed by flow cytometry for activation levels of blood neutrophils. As shown in FIG. 1, recombinant human C5a strongly stimulates the CD11b up-regulation on human neutrophils. This effect can completely be blocked in presence of the anti-human C5a antibody IFX-1. This inhibition is highly specific and the unspecific human IgG4 antibody did not show any blocking activity.

As a source for endogenous C5a (eC5a), zymosan-activated plasma (ZAP) from different donors was used to stimulate the blood neutrophils. The amount of eC5a production in the blood after stimulation with ZAP was measured using a commercial C5a-ELISA. The data presented here (FIG. 2) point out that stimulation of whole blood with eC5a in ZAP induced CD11b up-regulation comparable to rhC5a-induced CD11b up-regulation. The presence of IFX-1 significantly decreased the CD11b expression on human neutrophils, even at an Ab:Ag molar ratio of 0.5:1. The overall blocking activity of IFX-1 to ZAP-induced CD11b up-regulation ranged from 100% to 82% depending on the Ab:Ag ratio. Despite that the high level of eC3a and other complement activation products in ZAP are present in ZAP, IFX-1 could block CD11b upregulation up to 100%. It can therefore be concluded that eC5a is the sole driver for neutrophil activation upon ZAP stimulation, and IFX-1 can completely block it.

Figure 3:
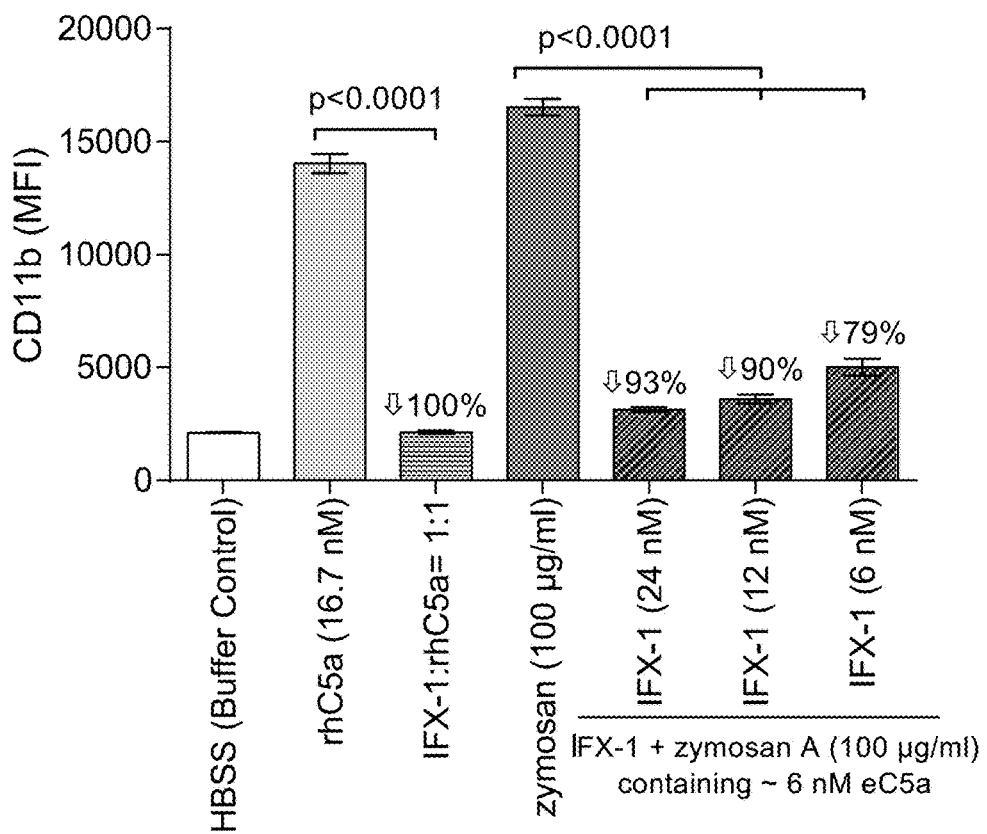
FIG. 3. Activation of blood neutrophils by zymosan and IFX-1 blocking activity. Whole blood was incubated with HBSS, rhC5a and zymosan A alone, or combinations of different IFX-1 concentrations and rhC5a or zymosan A. After incubation, cells were stained with anti-mouse CD11b: FITC, and CD11b MFI was analyzed by flow cytometry. Results are presented as mean±SD. The percentage of IFX-1 blocking activity of C5a-induced CD11b expression is marked (arrow). Statistical differences were calculated by One-Way-ANOVA, p values of p<0.05 were statistically significant.

2.2 C5a Blockade Attenuates Zymosan-Induced Inflammatory Responses in the Human Whole Blood Zymosan A, as an active fungus wall component, can induce strong inflammatory responses in the whole blood as characterized by activation of neutrophils and increased levels of cytokine and chemokines. In this study, human whole blood was spiked with zymosan A in the presence or absence of IFX-1, and CD11b on the blood neutrophils were measured by flow cytometric analysis. As shown in FIG. 3, CD11b on blood neutrophils was strongly upregulated when zymosan was spiked in the human whole blood. The increase of CD11b expression by zymosan stimulation can be suppressed by 79%-93% depending on the concentration of IFX-1 added. As a positive control, the CD11b up-regulation stimulated by rhC5a was 100% blocked by IFX-1. Therefore, it is affirmative that the CD11b up-regulation on blood neutrophils upon zymosan A stimulation is caused primarily by eC5a. In addition, it can be concluded that eC5a, once generated in the whole blood by zymosan A, binds to IFX-1 first, thereby blocking its access to its nature receptors.

Figure 4:
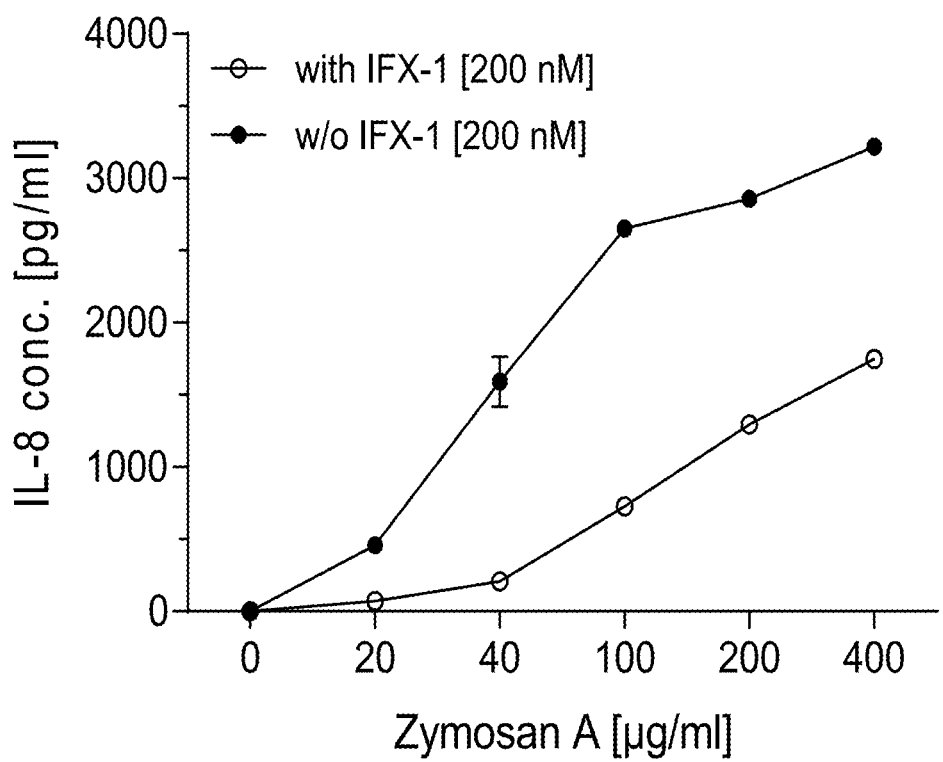
FIG. 4. IFX-1 inhibits zymosan-induced generation of IL-8 in human whole blood. IL-8 concentrations were obtained by ELISA after incubation of human whole blood with different zymosan A concentrations as indicated on the x-axis in the presence (empty circles) or absence (filled circles) of IFX-1. Results were presented as mean±SD.

In the same experimental set-up, IL-8 levels were measured and used to assess the inflammatory response as well. IL-8 concentrations after various doses of zymosan A stimulation ranged from 458 μg/ml to 3218 μg/ml in the absence of IFX-1. As shown in FIG. 4, the presence of IFX-1 significantly reduced IL-8 generation upon stimulation with various concentrations of zymosan A and the reduction rate up to 54% was observed. Thus, in the whole blood setting of inflammation zymosan-induced inflammatory responses are largely dependent on the presence of C5a.

3. Clinical Relevant Data

3.1 Data Obtained from Clinical Samples

3.1.1 Complement Activation in HS Patients

A total of 54 patients with HS and 14 healthy volunteers were enrolled in the study. Patients are under follow-up in the Outpatient Department of Immunology of Infectious Diseases of the ATTIKON University Hospital, Greece. The study was approved by the Ethics Committee of the hospital.

Written informed consent was provided by all patients. Diagnosis of HS was based on the following criteria: a) onset early after puberty; b) presence of subcutaneous nodules in areas of skin rich in apocrine glands; and c) a compatible history of recurrent drainage of pus from the affected areas.

Figure 5A:
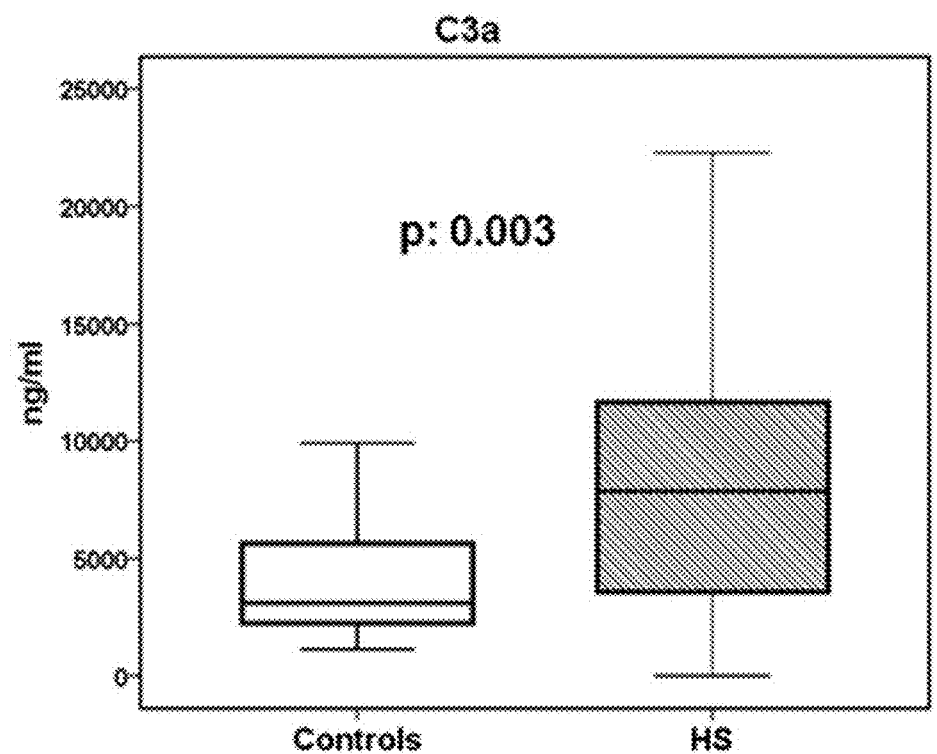
FIGS. 5A-5C. Concentrations of C3a (FIG. 5A), C5a (FIG. 5B) and C5b-9 (FIG. 5C) in the plasma of 14 healthy controls and of 54 patients with hidradenitis suppurativa (HS). Circles denote outliers and asterisks denote extremes. P values symbolize significant differences between patients and controls.
Figure 5B:
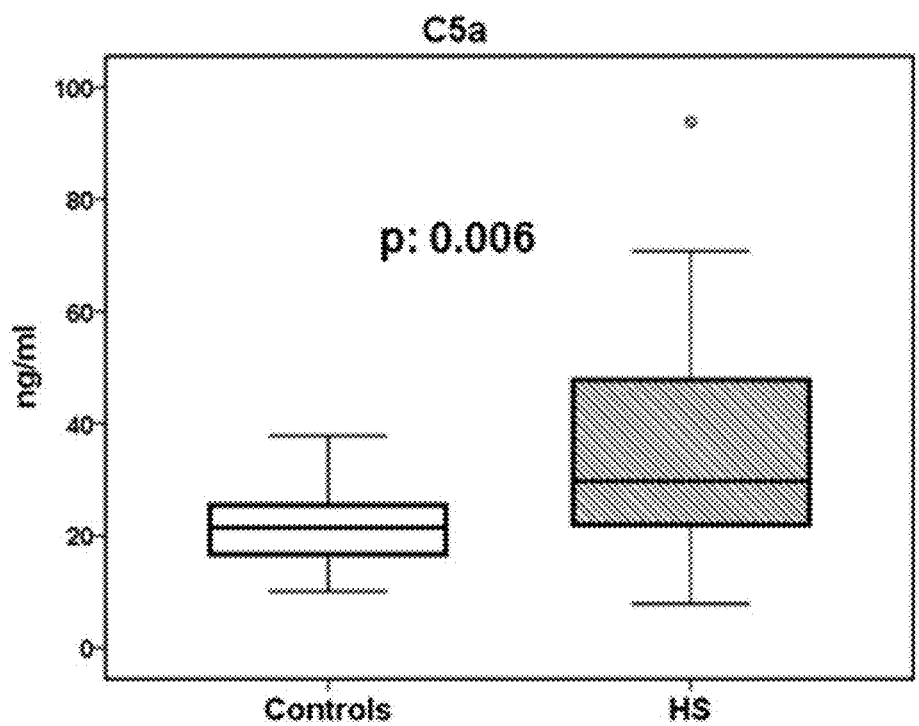
Figure 5C:
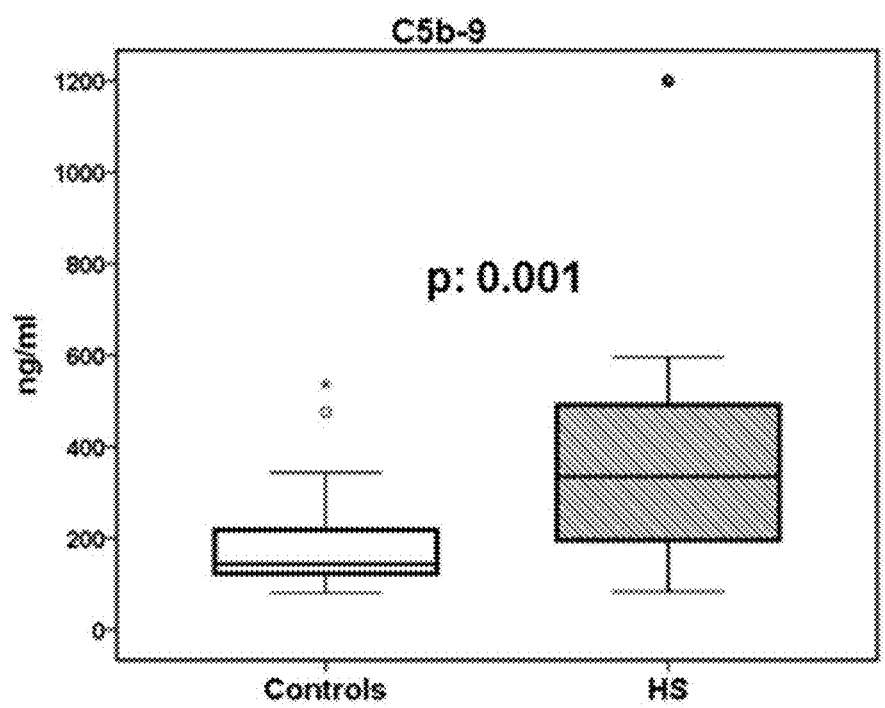

Circulating concentrations of complement factors C3a and C5a as well as membrane attack complex sC5b-9 were determined in the plasma of 54 patients and of 14 healthy controls as well as in the pus of seven patients. As shown in FIG. 5, circulating C5a was significantly greater in patient plasma than in control plasma (P<0.01), and differences of C3a and C5b-9 between patients and controls were of similar significance. Therefore, it can be concluded that systemic complement activation occurs in HS. Given the essential role of complement activation in the innate and adaptive immunity, the inventors assumed that targeting of complement activation could be a new therapeutic strategy for the treatment of HS.

However, from the above results it was not clear which one of C3a, C5a or C5-9b or other complement activation products would be the most promising target for this new therapeutic strategy and whether it would be sufficient to target only one of these factors or whether two or more factors involved in complement activation have to be targeted.

3.1.2 Blocking of CD11b Upregulation on Blood Neutrophils Induced by HS Plasma

Figure 6:
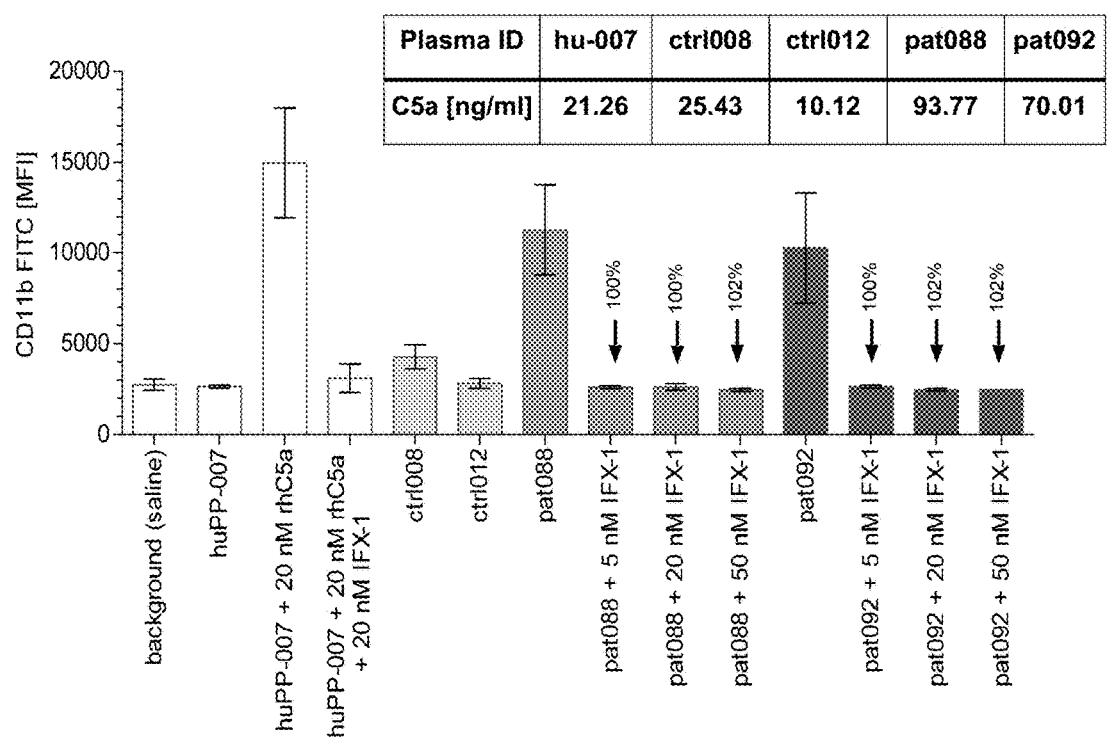
FIG. 6. Effect of HS plasma on blood neutrophil activation and the potential role of C5a. HS plasma samples were incubated with human plasma in the presence and absence of IFX-1, and CD11b expression on blood neutrophils was determined by flow cytometric analysis. C5a levels in the control and HS samples were labeled in the embedded table.
Figure 7:
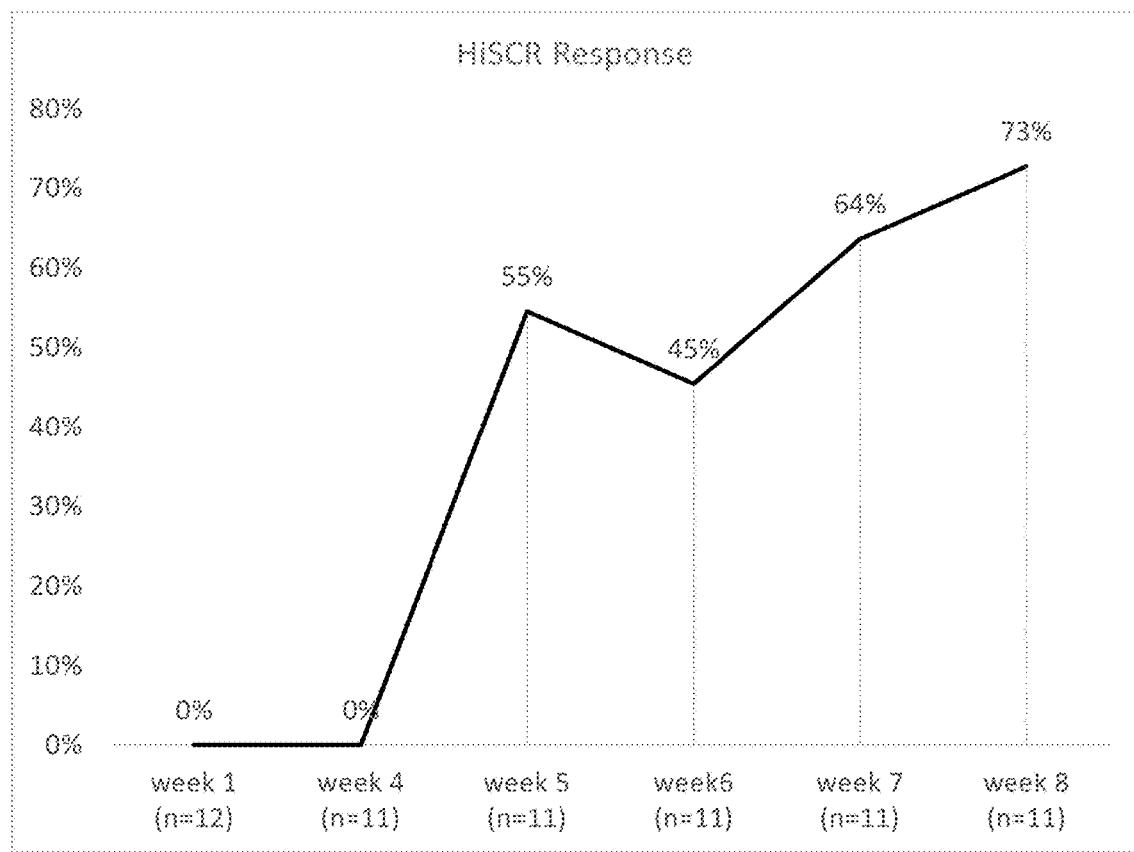
FIG. 7. HiSCR response post IFX-1 treatment in HS patients. HiSCR responder is defined as a ≥50% reduction in inflammatory lesion count (abscesses+inflammatory nodules), and no increase in abscesses or draining fistulas when compared with baseline.

To determine the role of C5a in the HS plasma sample on the neutrophil activation, the HS plasma samples with high levels of C5a were chosen and assessed by employing the human whole blood model. As shown in FIG. 6, in contrast to the control plasma samples with low C5a levels (Ctrl008 and Ctrl012), HS plasma samples (pat088 and pat092) with high levels of C5a strongly upregulated CD11b expression on the blood neutrophils. Recombinant human C5a was used as the positive control, while the plasma from healthy volunteers was chosen as the negative control. The CD11b upregulation induced by HS plasma can be 100% suppressed by IFX-1, indicating that C5a is the most important activator in the HS plasma to initiate the neutrophil activation. From these novel results the inventors concluded that blockade of C5a in HS patients is sufficient to achieve a strong suppression of the neutrophil activation.

3.2 Data Obtained from Clinical Trial 3.2.1 Trial Design

An open label Phase II trial in 11 patients with moderate to severe hidradenitis suppurativa was conducted in Department of Internal Medicine, ATTIKON University Hospital, Greece.

Primary objective of the trial was to explore the safety and tolerability of IFX-1 administered over 8 weeks. Secondary objectives of the trial were to assess the pharmacokinetics and pharmacodynamics of IFX-1 as well as to generate preliminary data on the efficacy of IFX-1 on clinical endpoints (e.g., HiSCR, DLQI, VAS for disease status, VAS for pain, HS-PGA, modified Sartorius Score) to generate further hypotheses. The enrolled patients were treated with 800 mg IFX-1 twice in the first week and once a week thereafter for the total 8-week treatment; i.e. IFX-1 was administered in nine intravenous doses of 800 mg IFX-1 on days 1, 4, 8, 15, 22, 29, 36, 43, and 50. All patients were followed up for 12 additional weeks.

Inclusion Criteria at Screening:
1. Male or female patients ≥18 years old
2. Written informed consent
3. Diagnosis of HS for at least 1 year
4. HS lesions in at least 2 distinct anatomic areas, one of which is Hurley Stage II or III
5. Total AN (abscesses and nodules) count ≥3
6. Patients with either primary or secondary failure of biological treatment or are not eligible for treatment with other biologicals
   NOTE: a primary failure is defined as an at least 12 week treatment with a biological compound without effect and a secondary failure as achieving an initial response after at least 12 week treatment with a biological compound followed by a relapse. 7. Failure of previous antimicrobial treatments Exclusion Criteria at Screening:
1. Body weight above 150 kg or body weight below 60 kg
2. Has a draining fistula count of greater than 30 at baseline
3. Surgical management planned within the next 24 weeks
4. Occurrence of a flare-up of HS leading to intravenous antimicrobial treatment within the last 14 days
5. Any other disease and condition that is likely to interfere with evaluation of study product, outcome assessment or satisfactory conduct of the study
   a) Active infection
   b) Severe congestive heart failure (i.e., NYHA Class IV)
   c) Depression
   d) History of systemic lupus erythematosus or rheumatoid arthritis
   e) Any immunodeficiency disease
   f) Active hematological or solid malignant tumor
   g) Patients must not have had any other active skin disease or condition (e.g., bacterial, fungal, or viral infection) that may have interfered with assessment of HS.
6. One of the following abnormal laboratory results
   a) White blood cell count <2,500/mm$^3$
   b) Neutrophil count <1000/mm$^3$
   c) Serum creatinine >3×Upper Normal Limit (UNL)
   d) Total bilirubin >2×UNL
   e) Alanine-Aminotransferase (ALAT) >2×UNL
   f) Positive screening test for Hepatitis B, Hepatitis C, or HIV 1/2
7. Prior administration of any biological compound in the last 3 months
8. Intake of corticosteroids defined as daily intake of prednisone or equivalent more than 1 mg/kg for the last three weeks;
9. Intake of immunosuppressive drugs within the past 30 days (e.g., cyclosporine, tacrolimus)
10. General exclusion criteria
    a) Pregnant (in women of childbearing potential an urine pregnancy test has to be performed) or breast-feeding women
    b) Women with childbearing potential (defined as within two years of their last menstruation) not willing to practice appropriate contraceptive measures (e.g., implanon, injections, oral contraceptives, intrauterine devices, partner with vasectomy, abstinence) while participating in the trial
    c) Participation in any interventional clinical trial within the last three months
    d) Known intravenous drug abuse
    e) Employee at the study site, spouse/partner or relative of any study staff (e.g., investigator, sub-investigators, or study nurse) or relationship to the sponsor

3.2.2 Clinical Trial Findings

IFX-1 is well tolerated in HS patients. There were no drug-related serious adverse events reported over the treatment period.

A commonly used efficacy parameter in the Hidradenitis Suppurativa Clinical Response (HiSCR). HiSCR is defined by the status of three types of lesions (defining criteria): abscesses (fluctuant, with or without drainage, tender or painful), inflammatory nodules (tender, erythematosus, pyogenic granuloma lesion) and draining fistulas (sinus tracts, with communications to skin surface, draining purulent fluid). The proposed definition of responders to treatment (HiSCR achievers) is: (i) at least a 50% reduction in ANs, (ii) no increase in the number of abscesses, and (iii) no increase in the number of draining fistulas from baseline. HiSCR has been validated recently as a responsive and clinically meaningful endpoint of the inflammatory manifestation of HS (Kimball and others, 2014).

The HiSCR response over the treatment period of 8 weeks was investigated in this study, and 8 out of 11 patients already treated up to Day 56 responded, which represents a response rate of 72.7% and a 95% confidence interval of 43% to 91%. To compare these results with historical data a literature search was performed to detect placebo controlled clinical studies that used HiSCR as an efficacy parameter. The following Table 4 summarizes the five studies that were completed recently:

TABLE 4

| Compound | N | Placebo responder n (%) | Comment |
|---|---|---|---|
| Adalimumab[1] | 13 | 2 (15%) | Post hoc analysis of Phase II trial. Only subgroup of patients with Hurley III |
| Adalimumab[1] | 70 | 15 (21%) | Study313, subgroup of patients with Hurley III |
| Adalimumab[1] | 76 | 13 (17%) | Study810, subgroup of patients with Hurley III |
| Anakinra[2] | 10 | 3 (30%) | All patients. 6 of 10 patients had Hurley III |
| MABp1[3] | 10 | 1 (10%) | Anti-TNFa treatment failures |

[1]Humira EMA assessment report http://www.ema.europa.eu/docs/en_GB/document_library/EPAR_-_Assessment_Report_-_Variation/human/000481/WC500195564.pdf
[2]Anakinra Study (Tzanetakou and others, 2016).
[3]Press release XBiotech (http://investors.xbiotech.com/phoenix.zhtml?c=253990&p=irol-newsArticle&ID=2246777)

In total, 179 patients have been treated in the placebo group of these studies with a response rate of 19.0% with a 95%-confidence interval of 14% to 25%. As both confidence intervals (e.g., the historical placebo patients and the patients treated with IFX-1) are not overlapping, a significant treatment effect of IFX-1 can be concluded.

Photographic documentation of the affected areas confirmed these findings by a highly reduced inflammation on the skin, as evidenced by the visual reduction of inflammatory swollenness and redness post treatment.

Thus, anti-C5a represents a powerful anti-inflammatory agent in the disease setting of HS. This clinical finding demonstrates that blockade of C5a is highly effective to reduce the activation of neutrophils thereby effectively alleviating cutaneous neutrophilic inflammatory disorders.

REFERENCES

Abi Abdallah D S, Egan C E, Butcher B A, Denkers E Y. 2011. Mouse neutrophils are professional antigen-presenting cells programmed to instruct Th1 and Th17 T-cell differentiation. Int Immunol 23(5):317-326.

Braun-Falco M, Kovnerystyy O, Lohse P, Ruzicka T. 2012. Pyoderma gangrenosum, acne, and suppurative hidradenitis (PASH)—a new autoinflammatory syndrome distinct from PAPA syndrome. J Am Acad Dermatol 66(3):409-415.

Cugno M, Borghi A, Marzano A V. 2017. PAPA, PASH and PAPASH Syndromes: Pathophysiology, Presentation and Treatment. Am J Clin Dermatol.

Czermak B J, Sarma V, Pierson C L, Warner R L, Huber-Lang M, Bless N M, Schmal H, Friedl H P, Ward P A. 1999. Protective effects of C5a blockade in sepsis. Nat Med 5(7):788-792.

Guo R F, Riedemann N C, Sun L, Gao H, Shi K X, Reuben J S, Sarma V J, Zetoune F S, Ward P A. 2006. Divergent signaling pathways in phagocytic cells during sepsis. J Immunol 177(2):1306-1313.

Guo R F, Ward P A. 2005. Role of C5a in inflammatory responses. Annu Rev Immunol 23:821-852.

Huber-Lang M S, Sarma J V, McGuire S R, Lu K T, Guo R F, Padgaonkar V A, Younkin E M, Laudes U, Riedemann N C, Younger J G and others. 2001. Protective effects of anti-C5a peptide antibodies in experimental sepsis. FASEB J 15(3):568-570.

Huber-Lang M S, Younkin E M, Sarma J V, McGuire S R, Lu K T, Guo R F, Padgaonkar V A, Curnutte J T, Erickson R, Ward P A. 2002. Complement-induced impairment of innate immunity during sepsis. J Immunol 169(6):3223-3231.

Jemec G B. 2004. Medical treatment of hidradenitis suppurativa. Expert Opin Pharmacother 5(8):1767-1770.

Jemec G B, Heidenheim M, Nielsen N H. 1996. The prevalence of hidradenitis suppurativa and its potential precursor lesions. J Am Acad Dermatol 35(2 Pt 1):191-194.

Kaplan M J. 2013. Role of neutrophils in systemic autoimmune diseases. Arthritis Res Ther 15(5):219.

Kimball A B, Jemec G B, Yang M, Kageleiry A, Signorovitch J E, Okun M M, Gu Y, Wang K, Mulani P, Sundaram M. 2014. Assessing the validity, responsiveness and meaningfulness of the Hidradenitis Suppurativa Clinical Response (HiSCR) as the clinical endpoint for hidradenitis suppurativa treatment. Br J Dermatol 171(6):1434-1442.

Kurzen H, Kurokawa I, Jemec G B, Emtestam L, Sellheyer K, Giamarellos-Bourboulis E J, Nagy I, Bechara F G, Sartorius K, Lapins J and others. 2008. What causes hidradenitis suppurativa? Exp Dermatol 17(5):455-456; discussion 457-472.

Lima A L, Karl I, Giner T, Poppe H, Schmidt M, Presser D, Goebeler M, Bauer B. 2016. Keratinocytes and neutrophils are important sources of proinflammatory molecules in hidradenitis suppurativa. Br J Dermatol 174(3):514-521.

Marzano A V. 2016. Hidradenitis suppurativa, neutrophilic dermatoses and autoinflammation: what's the link? Br J Dermatol 174(3):482-483.

Marzano A V, Ceccherini I, Gattorno M, Fanoni D, Caroli F, Rusmini M, Grossi A, De Simone C, Borghi O M, Meroni P L and others. 2014. Association of pyoderma gangrenosum, acne, and suppurative hidradenitis (PASH) shares genetic and cytokine profiles with other autoinflammatory diseases. Medicine (Baltimore) 93(27):e187.

Nemeth T, Mocsai A. 2012. The role of neutrophils in autoimmune diseases. Immunol Lett 143(1):9-19.

Nemeth T, Mocsai A, Lowell C A. 2016. Neutrophils in animal models of autoimmune disease. Semin Immunol 28(2):174-186.

Pawaria S, Ramani K, Maers K, Liu Y, Kane L P, Levesque M C, Biswas P S. 2014. Complement component C5a permits the coexistence of pathogenic Th17 cells and type I IFN in lupus. J Immunol 193(7):3288-3295.

Prat L, Bouaziz J D, Wallach D, Vignon-Pennamen M D, Bagot M. 2014. Neutrophilic dermatoses as systemic diseases. Clin Dermatol 32(3):376-388.

Revuz J. 2009. Hidradenitis suppurativa. J Eur Acad Dermatol Venereol 23(9):985-998.

Riedemann N C, Guo R F, Neff T A, Laudes I J, Keller K A, Sarma V J, Markiewski M M, Mastellos D, Strey C W, Pierson C L and others. 2002. Increased C5a receptor expression in sepsis. J Clin Invest 110(1):101-108.

Rittirsch D, Flierl M A, Nadeau B A, Day D E, Huber-Lang M, Mackay C R, Zetoune F S, Gerard N P, Cianflone K, Kohl J and others. 2008. Functional roles for C5a receptors in sepsis. Nat Med 14(5):551-557.

Slade D E, Powell B W, Mortimer P S. 2003. Hidradenitis suppurativa: pathogenesis and management. Br J Plast Surg 56(5):451-461.

Strainic M G, Shevach E M, An F, Lin F, Medof M E. 2013. Absence of signaling into CD4(+) cells via C3aR and C5aR enables autoinductive TGF-beta1 signaling and induction of Foxp3(+) regulatory T cells. Nat Immunol 14(2):162-171.

Tzanetakou V, Kanni T, Giatrakou S, Katoulis A, Papadavid E, Netea M G, Dinarello C A, van der Meer J W, Rigopoulos D, Giamarellos-Bourboulis E J. 2016. Safety and Efficacy of Anakinra in Severe Hidradenitis Suppurativa: A Randomized Clinical Trial. JAMA Dermatol 152(1):52-59.

Ward P A. 2009. Functions of C5a receptors. J Mol Med (Berl) 87(4):375-378.

Wollina U, Koch A, Heinig B, Kittner T, Nowak A. 2013. Acne inversa (Hidradenitis suppurativa): A review with a focus on pathogenesis and treatment. Indian Dermatol Online J 4(1):2-11.

Xu R, Wang R, Han G, Wang J, Chen G, Wang L, Li X, Guo R, Shen B, Li Y. 2010. Complement C5a regulates IL-17 by affecting the crosstalk between D C and gammadelta T cells in CLP-induced sepsis. Eur J Immunol 40(4):1079-1088.

What is claimed is:

1. A method of treating Hidradenitis suppurativa (HS) or a HS-related disease in a subject, the method comprising: administering to the subject in need thereof an effective amount of an agent that inhibits C5a activity in the subject, wherein the HS-related disease is selected from the group consisting of Pyoderma gangrenosum (PG); PASH (PG, acne and Hidradenitis suppurativa); and PAPASH (Pyogenic arthritis, acne, PG and Hidradenitis suppurativa).

2. The method of claim 1, wherein the agent inhibits C5a activity by one or more of: lowering the concentration of C5; inhibiting cleavage of C5 into C5a and C5b; lowering the concentration of C5a; inhibiting binding between C5a and a C5a receptor; lowering the concentration of a C5a receptor; or inhibiting the activity of a C5a receptor.

3. The method of claim 1, wherein the agent inhibits C5a activity, reduces expression of C5 protein or C5a receptor protein.

4. The method of claim 1, wherein the C5a receptor is selected from the group consisting of C5aR and C5L2.

5. The method of claim 1, wherein the agent that inhibits C5a activity is ALN-CC5 or Avacopan.

6. The method of claim 1, wherein the compound is administered at a dose of 800 mg once per week or at a dose of 800 mg twice per week.

7. A method of inhibiting the interaction of a C5a receptor with a C5a receptor ligand to treat Hidradenitis suppurativa (HS) or a HS-related disease in a subject, the method comprising administering to the subject an agent that specifically binds to C5, to the C5a receptor, or to the C5a receptor ligand, thereby inhibiting the interaction of the C5a receptor with the C5a receptor ligand and treating the disease, wherein the HS-related disease is selected from the group consisting of Pyoderma gangrenosum (PG); PASH (PG, acne and Hidradenitis suppurativa); and PAPASH (Pyogenic arthritis, acne, PG and Hidradenitis suppurativa).

8. The method of claim 7, wherein the agent is selected from the group consisting of an antibody or an antigen-binding fragment thereof, an antibody-like protein, an inhibitory variant of C5a, an inhibitory variant of a C5a receptor, a protein acting on the complement pathway, a peptide, a small molecule, an oligonucleotide and an aptamer.

9. The method of claim 5, wherein the agent that inhibits C5a activity is Avacopan.

10. A method of treating Hidradenitis suppurativa (HS) or an HS-related disease in a subject, the method comprising: administering to the subject in need thereof an agent that inhibits C5a activity in the subject in an effective amount to treat HS or the HS-related disease, wherein the agent is selected from the group consisting of Avacopan, IFX-1, INab708, MEDI-7814, ALXN-1007, Eculizumab, ALXN1210, LFG316, ALXN5500, Coversin, RA101495, NOX-D21, Zimura, and ALN-CCS; and wherein the HS-related disease is selected from the group consisting of Pyoderma gangrenosum (PG); PASH (PG, acne and Hidradenitis suppurativa); and PAPASH (Pyogenic arthritis, acne, PG and Hidradenitis suppurativa).

11. A method of treating Hidradenitis suppurativa (HS) in a subject, the method comprising: administering to the subject in need thereof an agent that inhibits C5a activity in the subject in an effective amount to treat HS, wherein the agent is selected from the group consisting of Avacopan, IFX-1, INab708, MEDI-7814, ALXN-1007, Eculizumab, ALXN1210, LFG316, ALXN5500, Coversin, RA101495, NOX-D21, Zimura, and ALN-CCS.

12. The method of claim 10, wherein the subject has Hidradenitis suppurativa (HS) and the agent that inhibits C5a activity in the subject is Avacopan or IFX-1.

13. The method of claim 11, wherein the agent that inhibits C5a activity in the subject is Avacopan or IFX-1.

14. The method of claim 10, wherein the subject has Hidradenitis suppurativa (HS) and the agent that inhibits C5a activity in the subject is Avacopan.

15. The method of claim 11, wherein the agent that inhibits C5a activity in the subject is Avacopan.

16. The method of claim 10, wherein the subject has Hidradenitis suppurativa (HS) and the agent that inhibits C5a activity in the subject is IFX-1.

17. The method of claim 11, wherein the agent that inhibits C5a activity in the subject is IFX-1.

18. A method of treating Hidradenitis suppurativa (HS) or a HS-related disease in a subject, the method comprising: administering to a subject in need thereof an effective amount of Avacopan to treat HS or the HS-related disease, wherein the HS-related disease is selected from the group consisting of Pyoderma gangrenosum (PG); PASH (PG, acne and Hidradenitis suppurativa); and PAPASH (Pyogenic arthritis, acne, PG and Hidradenitis suppurativa).

19. A method of treating Hidradenitis suppurativa (HS) or a HS-related disease in a subject, the method comprising: administering to a subject in need thereof an effective amount of IFX-1 antibody, or an antigen-binding fragment thereof, to treat HS or the HS-related disease, wherein the HS-related disease is selected from the group consisting of Pyoderma gangrenosum (PG); PASH (PG, acne and Hidradenitis suppurativa); and PAPASH (Pyogenic arthritis, acne, PG and Hidradenitis suppurativa).

* * * * *